United States Patent
Valet et al.

(10) Patent No.: US 6,706,215 B1
(45) Date of Patent: Mar. 16, 2004

(54) COATING COMPOSITIONS STABILIZED AGAINST DAMAGE BY LIGHT, HEAT AND OXYGEN

(75) Inventors: Andreas Valet, Binzen (DE); Jean-Luc Birbaum, Fribourg (CH); Gerhard Rytz, Neuchâtel (CH); Norbert Wüms, Ursen (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 08/880,383

(22) Filed: Jun. 23, 1997

Related U.S. Application Data

(62) Division of application No. 08/665,041, filed on Jun. 7, 1996, now Pat. No. 5,753,729, which is a continuation of application No. 08/241,429, filed on May 11, 1994, now abandoned.

(30) Foreign Application Priority Data

| May 17, 1993 | (CH) | ................................. 1496/93 |
| Dec. 1, 1993 | (CH) | ................................. 3573/93 |

(51) Int. Cl.$^7$ ........................................... C07D 239/26
(52) U.S. Cl. ...................... 252/402; 252/401; 252/405; 544/335
(58) Field of Search ............... 544/335; 252/401, 252/402, 405

(56) References Cited

U.S. PATENT DOCUMENTS

| 3,442,898 A | 5/1969 | Leuthl .................. 544/334 |
| 4,619,956 A | 10/1986 | Susi ........................ 524/87 |
| 4,895,981 A | 1/1990 | Reinert et al. ............... 8/565 |
| 5,073,278 A | 12/1991 | Schumacher et al. ....... 252/47.5 |
| 5,288,778 A | 2/1994 | Schmitter et al. ........... 524/100 |
| 5,298,067 A | 3/1994 | Valet et al. ................ 524/102 |
| 5,300,414 A | 4/1994 | Leppard et al. ............ 430/507 |
| 5,322,868 A | 6/1994 | Valet et al. ................. 524/89 |

FOREIGN PATENT DOCUMENTS

| EP | 0434608 | 6/1991 |
| GB | 1029045 | 5/1966 |

OTHER PUBLICATIONS

Chemical Abst. 9964, vol. 63, 1965.
Chemical Abst. 92:42766, 1980.
Chemical Abst. 63:9965b, 1965.
Chem. Abst. 116:849575, 1992.
Pure Appl. Chem. 36, 141 (1973).
Abst. J. Chem. 26, 443 (1973).
J. Heterocycl. Chem. 22, 1551 (1985).

*Primary Examiner*—Richard L. Raymond
(74) *Attorney, Agent, or Firm*—Tyler A. Stevenson

(57) ABSTRACT

Coatings comprising
  A) a binder based on an organic polymer and
  B) as stabilizer against damage by light, heat and oxygen, a 2-(2'-hydroxyphenyl)-1,3-pyrimidine of the formula I

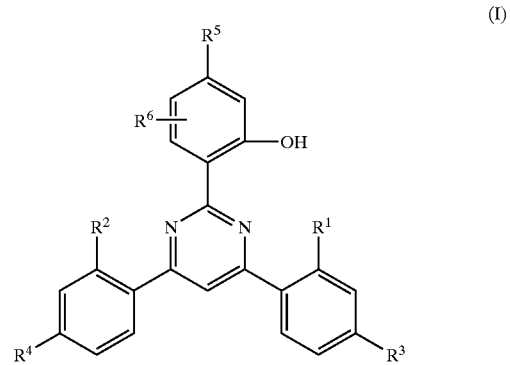

(I)

in which the radicals $R^1$ to $R^6$ are as defined in claim 1 have an outstanding resistance to the damaging effects of light, oxygen and heat. Compounds of the formula Ib defined in claim 18 are suitable in general for the stabilization of organic material.

12 Claims, No Drawings

COATING COMPOSITIONS STABILIZED AGAINST DAMAGE BY LIGHT, HEAT AND OXYGEN

This is a divisional of application Ser. No. 08/665,041, filed Jun. 7, 1996, now U.S. Pat. No. 5,753,729, which is a continuation of application Ser. No. 08/241,429, filed May 11, 1994, abandoned.

The invention relates to coating compositions stabilized against damage by light, heat and oxygen, which contain as stabilizer a 2-(2'-hydroxyphenyl)-1,3-pyrimidine derivative, to new compounds of the 2-(2'hydroxyphenyl)-1,3-pyrimidine type, to their use for stabilizing organic material and to corresponding compositions.

If it is desired to increase the light stability of an organic material, especially a coating, it is conventional to add a light stabilizer. One class of light stabilizers which is very frequently employed is that of the UV absorbers, which protect the material by absorbing the damaging radiation via chromophores. The most commonly used types of UV absorbers are 2-hydroxybenzophenones and 2-(2-hydroxyphenyl)benzotriazoles. In more recent literature, triphenyl-triazines are also mentioned as stabilizers for coating materials, for example in the publications U.S. Pat. No. 4,619,956, EP-A-434 608, EP-A-442 847 and EP-A-502 816, or as stabilizers for polycarbonate (U.S. Pat. No. 5,288,778).

Some o-hydroxy-substituted triphenylpyrimidines have also already been proposed as light stabilizers.

U.S. Pat. No. 3,442,898 describes the protective action of some compounds of this type against UV radiation in, for example, acetylcellulose, polyamide, polyvinyl chloride and polypropylene.

The teaching of U.S. Pat. No. 4,895,981 comprises their use as light stabilizers for polyester fibre materials.

Heller and Blattmann, Pure Appl. Chem. 36, 141 (1973) report on the use of some o-hydroxy-substituted triphenylpyrimidines in polyester. They come to the conclusion that these compounds, in polyester, have a comparatively small light stabilization effect and contribute to the accelerated discolouration of the substrate.

It has now been found that certain 2-(2'-hydroxyphenyl)-1,3-pyrimidine derivatives are surprisingly good stabilizers for coating compositions.

The invention relates to a coating composition comprising
A) a binder based on an organic polymer and
B) as stabilizer against damage by light, heat and oxygen, a compound of the formula I

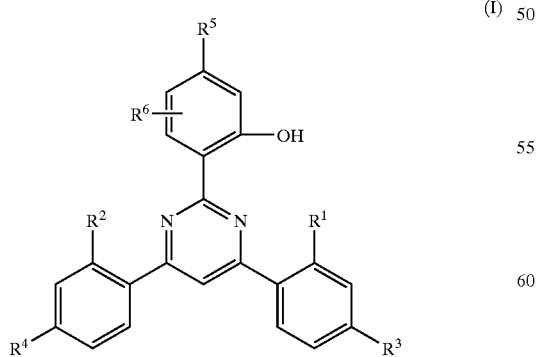

(I)

in which
$R^1$ and $R^2$ independently of one another are H; OH; $C_1-C_{12}$alkyl; cyclohexyl or trifluoromethyl;

$R^3$ and $R^4$ independently of one another have one of the definitions of $R^7$ or are $OR^7$ or halogen;
$R^5$ has one of the definitions given for $R^7$ or is halogen; —O—CO—$R^{12}$; —O—$SO_2$—$R^{13}$ or —O—$R^7$;
$R^6$ is H; $C_2-C_{18}$alkenyl; —X—$Z^3$; benzoyl which is unsubstituted or substituted on the phenyl ring by methyl, halogen, —CN or methoxy; —C($Z^3$)=N—$Z^3$; —CH($Z^3$)—NH—$Z^3$; a radical of the formula

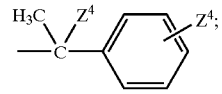

or a radical of the formula

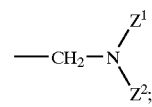

$R^7$ is hydrogen; $C_1-C_{18}$alkyl; $C_5-C_{18}$alkyloxycarbonyl; or $C_2-C_{18}$alkenyl; or $R^7$ is $C_1-C_{18}$alkyl which is substituted by OH, $C_1-C_{18}$alkoxy, $C_2-C_{18}$alkanoyl, $C_2-C_8$alkenyloxy, halogen, —COOH, —COO$R^8$, —CONH$_2$, —CONH$R^9$, —CON($R^9$)($R^{10}$), —NH$_2$, —NH$R^9$, —N($R^9$)($R^{10}$), —NHCO$R^{11}$, —CN, —OCO$R^{11}$, a group of the formula

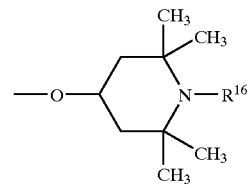

and/or phenoxy which is unsubstituted or is substituted by $C_1-C_{18}$alkyl, $C_1-C_{18}$alkoxy or halogen; or $R^7$ is $C_4-C_{20}$alkyl which is interrupted by O and substituted by OH or $C_1-C_{12}$alkoxy; glycidyl; $C_5-C_8$cycloalkyl; cyclohexyl which is substituted by OH, $C_1-C_4$alkyl or —OCO$R^{11}$; or $C_7-C_{11}$phenylalkyl which is unsubstituted or substituted by OH, Cl or $CH_3$;
$R^8$ is $C_1-C_{18}$alkyl; $C_2-C_6$hydroxyalkyl; $C_3-C_{18}$alkenyl; $C_3-C_{20}$alkyl which is interrupted by O, N or S and/or substituted by OH; $C_1-C_4$alkyl which is substituted by —P(O)(O$R^{14}$)$_2$, —N($R^9$)($R^{10}$) or —OCO$R^{11}$ and/or OH; glycidyl; cyclohexyl or $C_7-C_{11}$phenylalkyl; or is a group of the formula

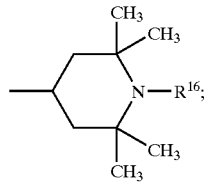

$R^9$ and $R^{10}$ independently of one another are $C_1-C_{12}$alkyl; $C_3-C_{12}$alkoxyalkyl; $C_4-C_{16}$dialkylaminoalkyl or $C_5-C_{12}$cycloalkyl or $R^9$ and $R^{10}$ together are $C_3-C_9$alkylene or -oxaalkylene or -azaalkylene;

$R^{11}$ is $C_1$–$C_{18}$alkyl; $C_2$–$C_{18}$alkenyl or phenyl;
$R^{12}$ is $C_1$–$C_{18}$alkyl; $C_2$–$C_{18}$alkenyl; phenyl; or —$R^{15}$—O—CO—$R^{11}$; or is a group of the formula

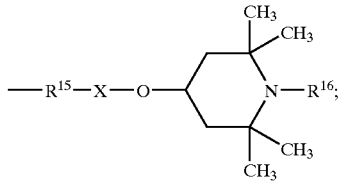

$R^{13}$ is $C_1$–$C_{12}$alkyl; phenyl; naphthyl or $C_7$–$C_{14}$alkylphenyl; and
$R^{14}$ is $C_1$–$C_{12}$alkyl or phenyl;
$R^{15}$ is $C_1$–$C_{18}$alkylene or $C_2$–$C_{18}$alkenylene;
$R^{16}$ is hydrogen; oxide; $C_1$–$C_8$alkanoyl; $C_1$–$C_{18}$alkyl; $C_2$–$C_{18}$-hydroxyalkyl; $C_3$–$C_{18}$hydroxyalkyl which is interrupted by O; $C_1$–$C_{18}$alkoxy; $C_5$–$C_8$cycloalkyl; $C_5$–$C_8$cycloalkoxy; $C_7$–$C_{11}$phenylalkyl; $C_7$–$C_{11}$phenylalkyl which is substituted on the phenyl ring by from 1 to 3 radicals $C_1$–$C_4$-alkyl or $C_1$–$C_8$alkanoyl; or $C_7$–$C_{11}$phenylalkoxy;
X is a direct bond or —CO—;
$Z^1$ and $Z^2$ independently of one another are $C_1$–$C_{12}$alkyl or together are $C_4$–$C_{10}$alkylene which may be interrupted by an oxygen atom;
$Z^3$ is $C_1$–$C_{20}$-Alkyl; and
$Z^4$ is hydrogen or methyl.

A halogen substituent is —F, —Cl, —Br or —I; it is preferably —Cl or —Br, especially —Cl.

In formula I the line protruding into the phenyl ring and carrying the symbol $R^6$ is a substituent which is located at one of the three remaining free positions, in the o-, m- or p-position to the phenolic OH group.

The substituent $R^6$ is preferably in the o- or p-position to the phenolic OH group, especially in the p-position.

$R^6$ includes, for example, hydrogen, $C_1$–$C_{12}$alkyl; $C_6$–$C_{18}$alkanoyl; benzoyl; methylbenzoyl; dimethylbenzoyl; benzoyl which is substituted by —Cl, —Br, —CN or —OCH$_3$; α-methylbenzyl; α,α-dimethylbenzyl; N,N-dialkylaminomethyl; 1-piperidylmethyl; 1-(4-oxapiperidyl)methyl; an imide of an acyl radical; and α-(N-alkylamino)alkyl. $R^6$ is preferably hydrogen, $C_1$–$C_6$alkyl, benzoyl, α-methylbenzyl, allyl or a radical of the formula

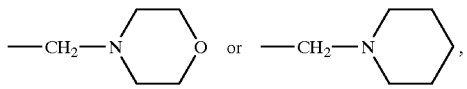

for example hydrogen or $C_1$–$C_6$-alkyl or allyl, particularly hydrogen or methyl and especially hydrogen.

Alkyl $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{16}$, $Z^1$ and $Z^2$ in the context of the definitions given is branched or unbranched alkyl such as methyl, ethyl, propyl, isopropyl, n-butyl, sec-butyl, isobutyl, t-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl and octadecyl. Alkyl $R^1$, $R^2$, $R^3$, $R^4$, $R^5$, $R^6$, $R^8$, $R^9$, $R^{10}$, $R^{11}$, $R^{12}$, $R^{13}$, $R^{14}$ and $R^{16}$ is preferably $C_1$–$C_8$alkyl, especially $C_1$–$C_4$alkyl such as methyl or tert-butyl, in particular methyl.

$R^6$ as alkanoyl is, for example, acetyl, propionyl, butyryl, valeryl, caproyl, caprylyl, caprinyl, lauroyl, myristyl, palmitoyl, or stearyl; $C_6$–$C_{18}$-alkanoyl is preferred.

Examples of $C_1$–$C_{18}$alkoxy $R^3$, $R^4$, $R^5$ and $R^{16}$ are methoxy, ethoxy, propoxy, isopropoxy, butoxy, isobutoxy, tert-butoxy, pentoxy, hexoxy, heptoxy, octyloxy, nonyloxy, decyloxy, undecyloxy, dodecyloxy, tridecyloxy, tetradecyloxy, pentadecyloxy, hexadecyloxy, heptadecyloxy or octadecyloxy; preference is given to $C_4$–$C_{12}$alkoxy, for example n-butoxy, n-pentoxy, n-hexoxy, n-heptoxy, n-octyloxy, 1-ethylhexyloxy, n-nonyloxy and n-decyloxy.

Substituted $C_1$–$C_{12}$alkyloxy $R^3$, $R^4$ and $R^5$ is preferably alkoxyalkyloxy, hydroxyalkyloxy interrupted by O, alkyloxy substituted by

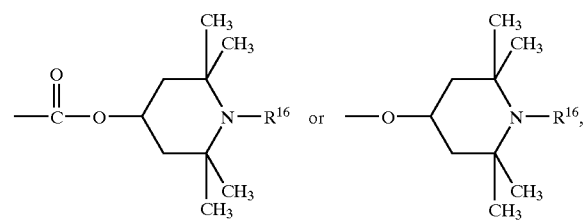

or alkyloxy which is substituted by alkenyloyloxy and/or hydroxyl; particularly interesting examples of $R^3$, $R^4$ and $R^5$ are —OCH$_2$CH$_2$OCOCH=CH$_2$, —OCH$_2$CH(OH)C$_8$H$_{17}$, —OCH$_2$CH(OH)C$_{12}$H$_{25}$, —OCH$_2$CH(OH)CH$_2$OC$_8$H$_{17}$, —OCH$_2$CH(OH)CH$_2$O—(CH$_2$)$_{12-14}$CH$_3$, —OCH$_2$CH(OH)CH$_2$OCOC(CH$_3$)=CH$_2$, —OCH$_2$CH(OH)CH$_2$OCOCH=CH$_2$,

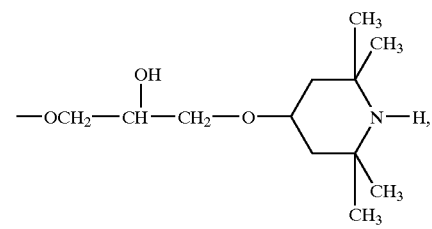

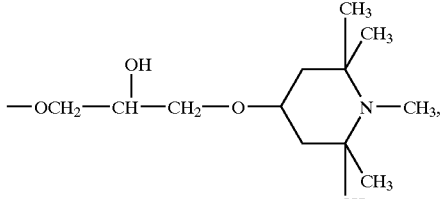

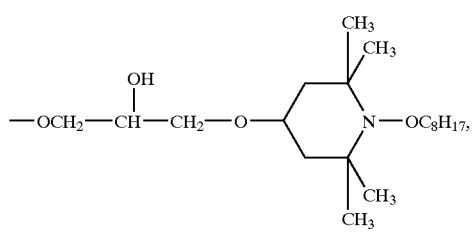

-continued

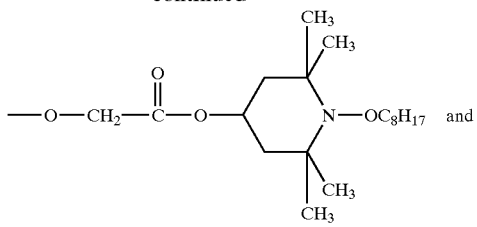 and

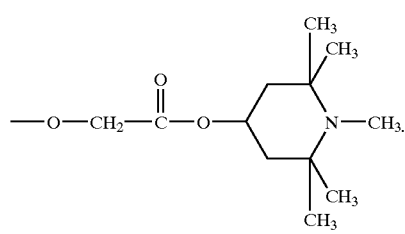

R¹, R², R³ and R⁴ are particularly preferably hydrogen or methyl. Of particular interest are compounds in which the radicals R¹, R², R³ and R⁴ are identical.

$C_3$–$C_{18}$-Alkenyl $R^7$, $R^8$, $R^{11}$ and $R^{12}$ comprises, inter alia, allyl, isopropenyl, 2-butenyl, 3-butenyl, isobutenyl, n-penta-2,4-dienyl, 3-methyl-but-2-enyl, n-oct-2-enyl, n-dodec-2-enyl, iso-dodecenyl, n-octadec-2-enyl and n-octadec-4enyl. For $R^7$, $R^{11}$ and $R^{12}$ the definition of vinyl is also possible. Alkenyl $R^{11}$ and $R^{12}$ is particularly preferably —CH=CH₂ or —C(CH₃)=CH₂.

Unsubstituted or substituted $C_5$–$C_8$cycloalkyl $R^7$ is for example cyclopentyl, cyclohexyl, cycloheptyl, cyclooctyl, methylcyclohexyl or acetyloxycyclohexyl; cyclohexyl is preferred.

$R^{16}$ is preferably hydrogen, $C_1$–$C_8$alkyl, $C_2$–$C_4$hydroxyalkyl, $C_1$–$C_{18}$alkoxy, $C_5$–$C_8$cycloalkoxy or substituted or unsubstituted $C_7$–$C_9$phenylalkyl; it is in particular hydrogen, methyl, $C_4$–$C_{12}$alkoxy, hydroxyethyl or cyclohexyloxy.

Cycloalkyloxy $R^{16}$ is preferably cyclohexyloxy; substituted or unsubstituted $C_7$–$C_{11}$phenylalkyl $R^{16}$ is preferably benzyl, α-methylbenzyl or methylphenyl-methyl.

Where alkyl radicals carry further substituents, or where individual radicals are alkylene, free valencies and bonds to substituents may extend from the same or from different carbon atoms. Bonds to heteroatoms preferably extend from different carbon atoms.

Consequently, substituted $C_1$–$C_{12}$alkyl $R^7$ is for example hydroxyalkyl such as 2-hydroxyethyl, 3-hydroxypropyl or 2-hydroxypropyl; alkoxyhydroxyalkyl such as 2-hydroxy-3-methoxypropyl, 2-hydroxy-3-ethoxypropyl, 2-hydroxy-3-butoxypropyl, 2-hydroxy-3-hexoxypropyl or 2-hydroxy-3-(2-ethylhexyloxy)propyl; alkoxycarbonylalkyl such as methoxycarbonylmethyl, ethoxycarbonylmethyl, butoxycarbonylmethyl, octyloxycarbonylmethyl, 1-octyloxycarbonyl-1-methylmethyl, 1-octyloxycarbonyl-1-ethylmethyl or 1-octyloxycarbonyl-1-hexylmethyl; or alkanoyloxyalkyl or alkenoyloxyalkyl such as 2-(acetyloxy) ethyl, 2-acryloxyethyl or 2-methacryloxyethyl; or for example 3-acryloxy- or 3-methacryloxy-2-hydroxypropyl.

$C_1$–$C_{18}$Alkylene $R^{15}$ is for example methylene, ethylene, propylene, butylene, pentylene, hexylene, heptylene, octylene, nonylene, decylene, undecylene, dodecylene, tridecylene, tetradecylene, pentadecylene, hexadecylene, heptadecylene, octadecylene; $C_2$–$C_{18}$alkylene or $C_4$–$C_{12}$alkenylene is preferred. Particular preference is given to terminal radicals, i.e. the free valencies are located at the ends of the longest carbon chain.

Preferred coating compositions are those in which the component (B) employed is a compound of the formula Ia

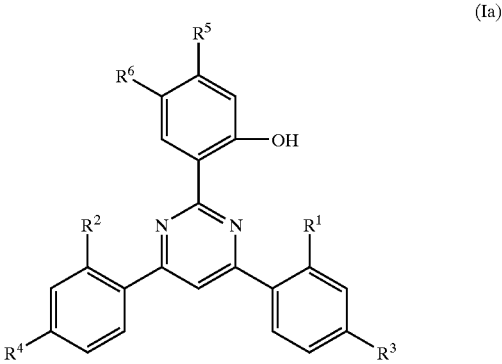

(Ia)

in which $R^3$ and $R^4$ independently of one another are —H; —OH; $C_1$–$C_{18}$alkoxy; —Cl; or —Br or may have one of the definitions of $R^7$;

$R^5$ has one of the definitions given for $R^7$ or is —Cl; —Br; —O—CO—$R^{12}$; or —O—$R^7$;

$R^7$ is $C_1$–$C_{18}$alkyl; or $C_3$–$C_{18}$alkenyl; or $R^7$ is $C_1$–$C_{12}$alkyl which is substituted by —OH, $C_1$–$C_{18}$alkoxy, —COOR⁸, —NHCOR¹¹, —CN, —OCOR¹¹, a group of the formula

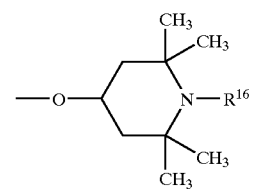

and/or phenoxy; or $R^7$ is $C_4$–$C_{20}$alkyl which is interrupted by from 1 to 6 —O— and substituted by —OH or $C_1$–$C_{12}$alkoxy; glycidyl; $C_5$–$C_8$cycloalkyl; or $C_7$–$C_{11}$phenylalkyl;

$R^8$ is $C_1$–$C_{18}$alkyl; $C_2$–$C_6$hydroxyalkyl; $C_3$–$C_{18}$alkenyl; or is a group of the formula

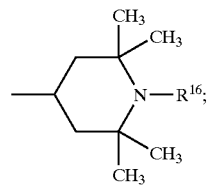

$R^{11}$ is $C_1$–$C_{18}$alkyl or $C_2$–$C_{18}$alkenyl;

$R^{12}$ is $C_1$–$C_{18}$alkyl; $C_2$–$C_{18}$alkenyl; or —$R^{15}$—O—CO—$R^{11}$; or is a group of the formula

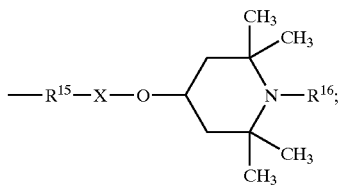

$R^{15}$ is $C_1$–$C_{18}$alkylene or $C_4$–$C_{18}$alkenylene; and
$R^{16}$ is hydrogen; $C_2$–$C_8$alkanoyl; $C_1$–$C_{12}$alkyl; $C_1$–$C_{12}$alkoxy; $C_5$–$C_8$cycloalkyl; $C_5$–$C_8$cycloalkoxy; or $C_7$–$C_{11}$phenylalkyl.

The compounds of the formula I which are particularly preferably used as component (B) are those in which
$R^1$ is hydrogen or OH or $C_1$–$C_4$alkyl; and $R^2$ is hydrogen or $C_1$–$C_4$alkyl;
$R^3$ and $R^4$ independently of one another are hydrogen or —OH or have one of the definitions of $R^7$ or are $OR^7$;
$R^5$ has one of the definitions given for $R^7$ or is Cl; —Br; —O—CO—$R^{12}$; or —O—$R^7$;
$R^6$ is hydrogen or $C_1$–$C_6$alkyl or allyl;
$R^7$ is $C_1$–$C_{18}$alkyl; or $C_3$–$C_{18}$alkenyl; or $R^7$ is $C_1$–$C_{12}$alkyl which is substituted by —OH, $C_1$–$C_{18}$alkoxy, —COOR$^8$, a group of the formula

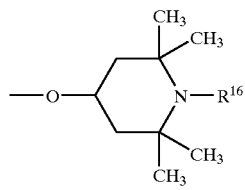

and/or —OCOR$^{11}$; or $R^7$ is $C_7$–$C_{18}$alkyl which is interrupted by from 1 to 6 —O— and substituted by —OH; $C_5$–$C_8$cycloalkyl; or $C_7$–$C_{11}$phenylalkyl;
$R^8$ is $C_1$–$C_{18}$alkyl; $C_2$–$C_6$hydroxyalkyl; or $C_3$–$C_{18}$alkenyl; or is a group of the formula

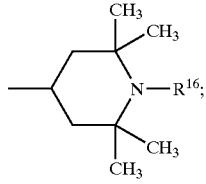

$R^{11}$ is $C_1$–$C_{18}$alkyl or $C_2$–$C_{18}$alkenyl;
$R^{12}$ is $C_1$–$C_{18}$alkyl; $C_2$–$C_{18}$alkenyl; —$R^{15}$—O—CO—CH=CH$_2$; or —$R^{15}$—O—CO—C(CH$_3$)=CH$_2$; or is a group of the formula

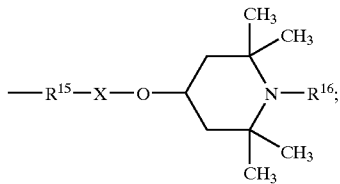

$R^{15}$ is $C_2$–$C_{18}$alkylene; and
$R^{16}$ is hydrogen; oxide; $C_2$–$C_8$alkanoyl; $C_1$–$C_{12}$alkyl; hydroxyethyl; $C_1$–$C_{12}$alkoxy; $C_5$–$C_8$cycloalkyl; $C_5$–$C_8$cycloalkoxy; or $C_7$–$C_{11}$phenylalkyl.

Among such compounds, particular preference is given to those in which
$R^1$ and $R^2$ independently of one another are hydrogen or methyl;
$R^3$ and $R^4$ independently of one another are hydrogen; methyl; or $C_1$–$C_{12}$alkyl which is substituted by —OH, $C_1$–$C_{18}$alkoxy, —COOR$^8$ and/or —OCOR$^{11}$; or are $C_1$–$C_{12}$alkoxy which is substituted by —OH, $C_1$–$C_8$alkoxy, —COOR$^8$ and/or —OCOR$^{11}$;
$R^5$ is $C_1$–$C_{18}$alkyl; $C_3$–$C_{18}$alkenyl; —Cl; —Br; —O—CO—$R^{12}$; or —O—$R^7$;
$R^6$ is hydrogen or $C_1$–$C_6$alkyl or allyl;
$R^7$ is $C_1$–$C_{18}$alkyl; or $C_3$–$C_{18}$alkenyl; or $R^7$ is $C_1$–$C_{12}$alkyl which is substituted by —OH, $C_1$–$C_{18}$alkoxy, —COOR$^8$, a group of the formula

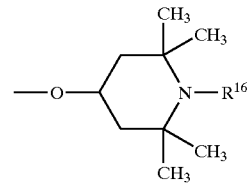

and/or —OCOR$^{11}$; or $R^7$ is $C_7$–$C_{18}$alkyl which is interrupted by from 1 to 3 —O— and substituted by —OH;
$R^{16}$ is hydrogen; acetyl; $C_1$–$C_8$alkyl; $C_4$–$C_{12}$alkoxy; $C_5$–$C_8$cycloalkyl; $C_5$–$C_8$cycloalkoxy; or benzyl.

A particularly emphatic interest is shown in coating compositions comprising as component (B) a compound of the formula I in which $R^1$ and $R^2$ independently of one another are hydrogen or methyl; $R^3$ and $R^4$ independently of one another are hydrogen, methyl or methoxy and $R^6$ is hydrogen.

Of outstanding interest as component (B) are compounds of the formula I in which
$R^1$ and $R^2$ are identical and are hydrogen or methyl;
$R^3$ and $R^4$ are identical and are hydrogen or methyl or methoxy;
$R^5$ is —O—$R^7$;
$R^6$ is hydrogen;
$R^7$ is $C_1$–$C_{18}$alkyl; or $R^7$ is $C_1$–$C_{12}$alkyl which is substituted by —OH, $C_1$–$C_{18}$alkoxy, —COOR$^8$, —OCOR$^{11}$ and/or a group of the formula

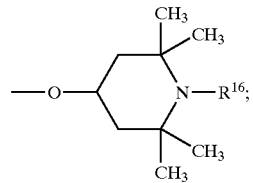

$R^8$ is $C_1$–$C_{12}$alkyl; and
$R^{11}$ is $C_1$–$C_{12}$alkyl.

The coating composition according to the invention preferably comprises 0.01–10 parts by weight of B, in particular 0.05–10 parts by weight of B and especially 0.1–5 parts by weight of B per 100 parts by weight of solid binder A.

A suitable binder (component A) may in principle be any of those common in industry, for example those as described in Ullmann's Encyclopedia of Industrial Chemistry, 5th Ed., Vol. A18, pp. 368–426, VCH, Weinheim 1991. In general it is a film-forming binder based on a thermoplastic or thermosettable resin, predominantly on a thermosettable resin. Examples of these are alkyd, acrylic, polyester, phenolic, melamine, epoxy and polyurethane resins and mixtures thereof.

Component A may be a cold-curable or a heat-curable binder; the addition of a curing catalyst may be advantageous. Examples of catalysts suitable for accelerating the curing of the binder are described in Ullmann's Encyclopedia of Industrial Chemistry, Vol. A 18, p. 469, VCH Verlagsgesellschaft, Weinheim 1991.

Preferred coating compositions are those in which component A is a binder comprising a functional acrylate resin and a crosslinking agent Examples of coating compositions containing specific binders are:

1. coating materials based on cold- or hot-crosslinkable alkyd, acrylate, polyester, epoxy or melamine resins or mixtures of these resins, with or without the addition of a curing catalyst;
2. two-component polyurethane coating materials based on hydroxyl group-containing acrylate, polyester or polyether resins and aliphatic or aromatic polyisocyanates;
3. one-component polyurethane coating materials based on blocked polyisocyanates which are deblocked during the baking procedure;
4. two-component coating materials based on (poly) ketimines and aliphatic or aromatic polyisocyanates;
5. two-component coating materials based on (poly) ketimines and an unsaturated acrylate resin or a polyacetoacetate resin or a methacrylamidoglycolate methyl ester,
6. two-component coating materials based on carboxyl or amino group-containing polyacrylates and polyepoxides;
7. two-component coating materials based on anhydride group-containing acrylate resins and a polyhydroxy or polyamino component;
8. two-component coating materials based on (poly) oxazolines and anhydride group-containing acrylate resins or unsaturated acrylate resins or aliphatic or aromatic polyisocyanates;
9. two-component coating materials based on unsaturated polyacrylates and polymalonates;
10. thermoplastic polyacrylate coating materials based on thermoplastic acrylate resins or acrylate resins which crosslink under the action of external crosslinking agents, in combination with etherified melamine resins;
11. coating systems based on siloxane-modified or fluorine-modified acrylate resins.

The coating compositions according to the invention may also be radiation-curable coating compositions. In this case the binder essentially comprises monomeric or oligomeric compounds having ethylenically unsaturated bonds, which are cured after application by UV radiation or electron beams, i.e. are converted into a crosslinked, high molecular weight form. Corresponding systems are described in the abovementioned publication, Ullmann's Encyclopedia of Industrial Chemistry, 5th Ed., Vol. A18, pages 451–453. In radiation-curable coating compositions the compounds of the formula I may also be employed without the addition of sterically hindered amines.

The coating composition according to the invention preferably contains—in addition to components A and B—as component C, a light stabilizer of the sterically hindered amine and/or 2-hydroxyphenyl-2H-benzotriazole type, such as, for example, those given in the list below under headings 2.1 and 2.6.

In order to achieve maximum light resistance, the addition of sterically hindered amines as given in the stated list under 2.6, is of special advantage. The invention therefore also relates to a coating composition which contains in addition to components A and B, as component C, a light stabilizer of the sterically hindered amine type.

It is preferably a 2,2,6,6-tetraalkylpiperidine derivative which contains at least one group of the formula

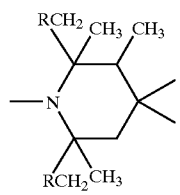

in which R is hydrogen or methyl, especially hydrogen.

Component C is preferably used in a quantity of 0.05–5 parts by weight per 100 parts by weight of the solid binder.

Examples of tetraalkylpiperidine derivatives which can be used as component C are given in U.S. Pat. No. 5,073,278; of special importance are those listed in columns 3–21 under sections a) to f). The sections of this patent document indicated are considered part of this description. It is particularly expedient to employ the following tetraalkylpiperidine derivatives:

bis(2,2,6,6-tetramethylpiperid-4-yl)succinate,
bis(2,2,6,6-tetramethylpiperid-4-yl)sebacate,
bis(1,2,2,6,6-pentamethylpiperid-4yl)sebacate,
di(1,2,2,6,6-pentamethylpiperid-4-yl)butyl(3,5-di-tert-butyl-4-hydroxybenzyl)malonate,
bis(1-octyloxy-2,2,6,6-tetramethylpiperid-4-yl)sebacate,
tetra(2,2,6,6-tetramethylpiperid-4-yl)butane-1,2,3,4-tetracarboxylate,
tetra(1,2,2,6,6-pentamethylpiperid-4-yl)butane-1,2,3,4-tetracarboxylate,
2,2,4,4-tetramethyl-7-oxa-3,20-diaza-21-oxodispiro[5.1.11.2]heneicosane,
8-acetyl-3-dodecyl-1,3,8-triaza-7,7,9,9-tetramethylspiro[4.5]decane-2,4-dione,
or a compound of the formulae

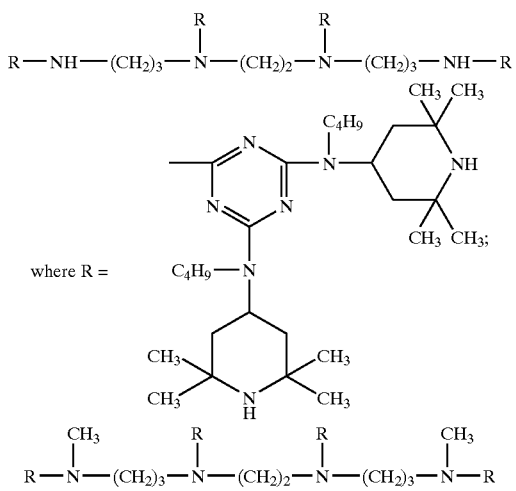

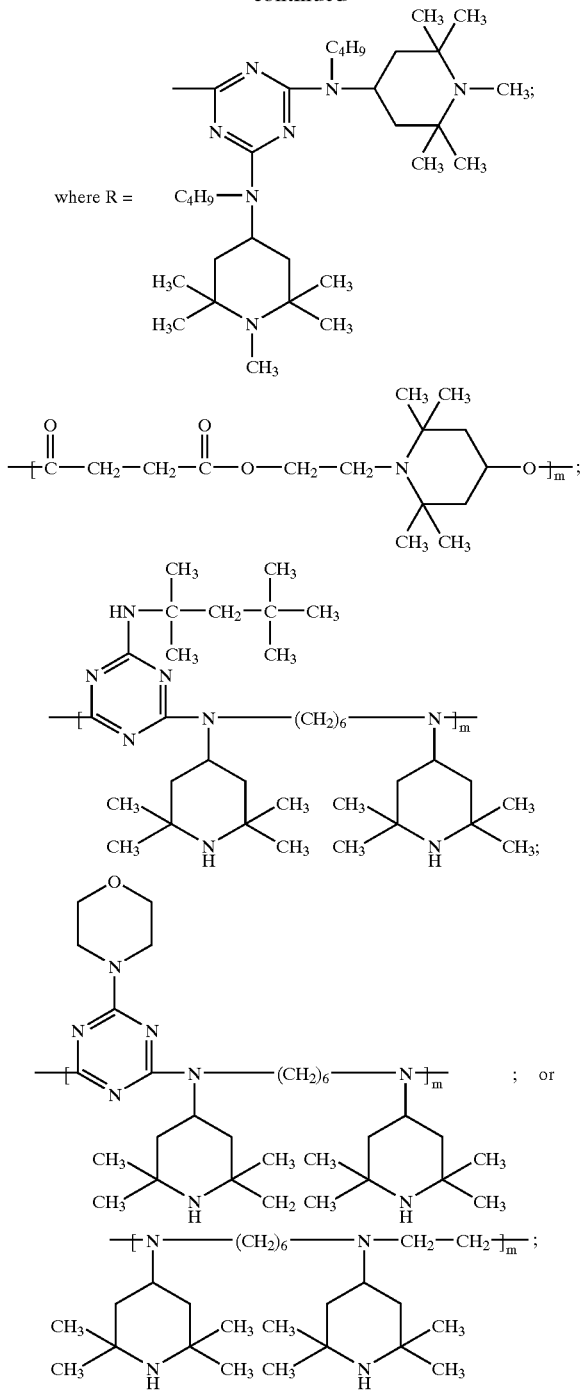

where m is 5–50.

In addition to components A and B, the coating composition may also contain further components, for example solvents, pigments, dyes, plasticizers, stabilizers, thixotropic agents, drying catalysts and/or levelling assistants. Examples of possible components are those described in Ullmann's Encyclopedia of Industrial Chemistry, 5th Ed., Vol. A18, pp. 429–471, VCH, Weinheim 1991.

Examples of possible drying catalysts or curing catalysts are organometallic compounds, amines, resins containing amino groups, and/or phosphines. Organometallic compounds are, for example, metal carboxylates, especially those of the metals Pb, Mn, Co, Zn, Zr or Cu, or metal chelates, especially those of the metals Al, Ti or Zr, or organometallic compounds such as organotin compounds.

Examples of metal carboxylates are the stearates of Pb, Mn or Zn, the octanoates of Co, Zn or Cu, the naphthenates of Mn and Co or the corresponding linoleates, resinates or tallates.

Examples of metal chelates are the aluminium, titanium or zirconium chelates of acetylacetone, ethyl acetoacetate, salicylaldehyde, salicylaldoxime, o-hydroxyacetophenone or ethyl trifluoroacetoacetate and the alkoxides of these metals.

Examples of organotin compounds are dibutyltin oxide, dibutyltin dilaurate or dibutyltin dioctanoate.

Examples of amines are in particular tertiary amines such as tributylamine, triethanolamine, N-methyldiethanolamine, N-dimethylethanolamine, N-ethylmorpholine, N-methylmorpholine or diazabicyclooctane (triethylenediamine) and their salts. Other examples are quaternary ammonium salts, for example trimethylbenzylammonium chloride.

Resins containing amino groups are simultaneously binder and curing catalyst. Examples of these are acrylate copolymers which contain amino groups.

The curing catalyst used can also be a phosphine, for example triphenylphosphine.

The coating compositions according to the invention can be applied to any desired substrates, for example to metal, wood, plastic or ceramic materials. They are preferably used as topcoat in the finishing of cars. If the topcoat consists of two coats, the bottom coat being pigmented and the upper coat being non-pigmented, then the coating composition according to the invention can be used for the upper or the bottom coat or for both coats, but preferably for the upper coat.

The coating compositions according to the invention can be applied to the substrates by the conventional methods, for example by brushing, spraying, flowcoating, dipping or electrophoresis; see also Ullmann's Encyclopedia of Industrial Chemistry, 5th Ed., Vol. A18, pp. 491–500.

Depending on the binder system the coatings can be cured at room temperature or by heating. The coatings are preferably cured at 50–150° C.; higher temperatures may be employed for powder coatings.

The coatings obtained in accordance with the invention have an outstanding resistance to the damaging effects of light, oxygen and heat; in particular, reference should be made to the good lightfastness and weathering resistance of the resulting coatings, for example paints.

The invention therefore relates also to a coating, in particular a varnish, which is stabilized by containing the compound of the formula I according to the invention against damaging effects of light, oxygen and heat. The varnish is preferably a topcoat for cars. The invention also relates to a method of stabilizing a coating based on organic polymers against damage by light, oxygen and/or heat, which comprises admixing with the coating composition a compound of the formula I, and to the use of compounds of the formula I in coating compositions as stabilizers against damage by light, oxygen and/or heat.

In a further embodiment of the method, the binders used are those in which a compound of the formula I is incorporated by copolymerization or copolycondensation. Compounds suitable for this purpose are those of the formula I in which the radical $R^5$ contains a copolymerizable, ethylenically unsaturated group or a functional group suitable for copolycondensation. In this case the coating composition can only comprise component A.

The coating compositions usually contain an organic solvent or solvent mixture in which the binder is soluble. The coating composition may, however, also be an aqueous solution or dispersion. The vehicle may also be a mixture of an organic solvent and water. The coating composition may also be a high-solids coating or can be solvent-free (powder coating).

The pigments can be inorganic, organic or metallic pigments. The coating compositions according to the invention preferably contain no pigments and are used as clearcoat.

A likewise preferred use of the coating composition is as a topcoat for applications in the automotive industry, especially as the pigmented or non-pigmented topcoat of the coating system. However, its use for underlying layers is also possible.

Some of the compounds of the formula I described above as component (B) are new compounds. The invention consequently also relates to compounds of the formula Ib

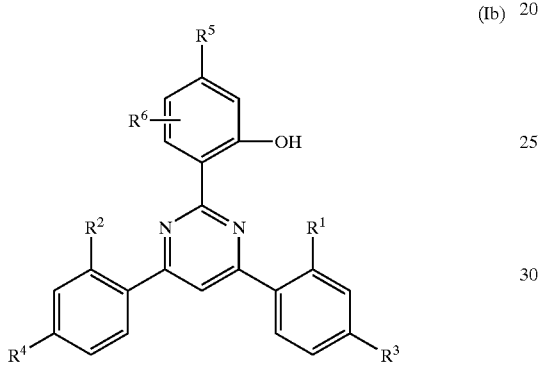

in which $R^1$ and $R^2$ independently of one another are H; OH; $C_1$–$C_{12}$alkyl; cyclohexyl or trifluoromethyl;

$R^3$ and $R^4$ independently of one another are hydrogen; —OH; $C_1$–$C_3$alkyl; $C_1$–$C_3$alkoxy; or halogen or have one of the definitions of $R^7$ or are $OR^7$;

$R^5$ has one of the definitions given for $R^7$ or is halogen; $C_1$–$C_3$alkyl; —O—CO—$R^{12}$; —O—$SO_2$—$R^{13}$ or —O—$R^7$;

$R^6$ is H; $C_2$–$C_{18}$alkenyl; —X—$Z^3$; benzoyl which is unsubstituted or substituted on the phenyl ring by methyl, halogen, —CN or methoxy; —C($Z^3$)=N—$Z^3$; —CH($Z^3$)—NH—$Z^3$; a radical of the formula

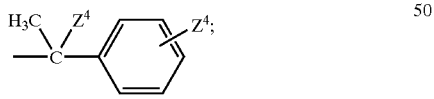

or a radical of the formula

$R^7$ is $C_4$–$C_{18}$alkyl or $C_2$–$C_{18}$alkenyl or $C_5$–$C_{18}$alkyloxycarbonyl; or $R^7$ is $C_1$–$C_{18}$alkyl which is substituted by OH, $C_1$–$C_{18}$alkoxy, $C_2$–$C_{18}$alkanoyl, halogen, —COOH, —COO$R^8$, —CONH$_2$, —CONH$R^9$, —CON($R^9$)($R^{10}$), —NH$_2$, —NH$R^9$, —N($R^9$)($R^{10}$), —NHCO$R^{11}$, —CN, —OCO$R^{11}$, a group of the formula

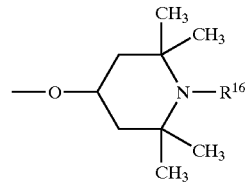

and/or phenoxy which is unsubstituted or is substituted by $C_1$–$C_{18}$alkyl, $C_1$–$C_{18}$alkoxy or halogen; or $R^7$ is $C_4$–$C_{20}$alkyl which is interrupted by O and substituted by OH or $C_1$–$C_{12}$alkoxy; glycidyl; $C_5$–$C_8$cycloalkyl; cyclohexyl which is substituted by OH, $C_1$–$C_4$alkyl or —OCO$R^{11}$; or $C_7$–$C_{11}$-phenylalkyl which is unsubstituted or substituted by OH, Cl or $CH_3$;

$R^8$ is $C_1$–$C_{18}$alkyl; $C_2$–$C_6$hydroxyalkyl; $C_3$–$C_{18}$alkenyl; $C_3$–$C_{20}$alkyl which is interrupted by O, N or S and/or substituted by OH; $C_1$–$C_4$alkyl which is substituted by —P(O)(O$R^{14}$)$_2$, —N($R^9$)($R^{10}$) or —OCO$R^{11}$ and/or OH; glycidyl; cyclohexyl or $C_7$–$C_{11}$phenylalkyl; or is a group of the formula

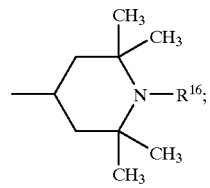

$R^9$ and $R^{10}$ independently of one another are $C_1$–$C_{12}$alkyl; $C_3$–$C_{12}$alkoxyalkyl; $C_4$–$C_{16}$dialkylaminoalkyl or $C_5$–$C_{12}$cycloalkyl or $R^9$ and $R^{10}$ together are $C_3$–$C_9$alkylene or -oxaalkylene or -azaalkylene;

$R^{11}$ is $C_1$–$C_{18}$alkyl; $C_2$–$C_{18}$alkenyl or phenyl;

$R^{12}$ is $C_1$–$C_{18}$alkyl; $C_2$–$C_{18}$alkenyl; phenyl; or —$R^{15}$—O—CO—$R^{11}$; or is a group of the formula

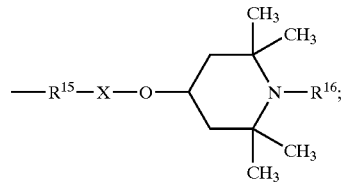

$R^{13}$ is $C_1$–$C_{12}$alkyl; phenyl; naphthyl or $C_7$–$C_{14}$alkylphenyl; and $R^{14}$ is $C_1$–$C_{12}$alkyl or phenyl;

$R^{15}$ is $C_1$–$C_{18}$alkylene or $C_2$–$C_{18}$alkenylene;

$R^{16}$ is hydrogen; oxide; $C_1$–$C_8$alkanoyl; $C_1$–$C_{18}$alkyl; $C_2$–$C_{18}$hydroxyalkyl; $C_3$–$C_{18}$hydroxyalkyl which is interrupted by O; $C_1$–$C_{18}$-alkoxy; $C_5$–$C_8$cycloalkyl; $C_5$–$C_8$-cycloalkoxy; $C_7$–$C_{11}$phenylalkyl; $C_7$–$C_{11}$phenylalkyl which is substituted on the phenyl ring by from 1 to 3 radicals $C_1$–$C_4$alkyl or $C_1$–$C_8$alkanoyl; or $C_7$–$C_{11}$phenylalkoxy;

X is a direct bond or —CO—;

$Z^1$ and $Z^2$ independently of one another are $C_1$–$C_{12}$alkyl or together are $C_4$–$C_{10}$alkylene which may be interrupted by an oxygen atom;

$Z^3$ is $C_1$–$C_{20}$-Alkyl; and $Z^4$ is hydrogen or methyl;

with the exception of a compound of the formula I in which 2 of the radicals $R^3$, $R^4$ and $R^5$ are alkoxy and the third radical has a definition other than alkoxy.

The preferred definitions of the radicals to $R^1$ to $R^{16}$ in the compounds of the formula Ib are essentially the same as those for the corresponding radicals in the compounds of the formula I.

In compounds of the formula Ib, $R^1$, $R^2$, $R^3$ and $R^4$ independently of one another are preferably H, $C_1$–$C_4$alkoxy or $C_1$–$C_4$alkyl, especially H or methyl.

$R^5$ in compounds of the formula Ib is preferably —O—$R^7$.

Preferred compounds of the formula Ib are those in which $R^1$ and $R^2$ independently of one another are H; OH; $C_1$–$C_{12}$alkyl; cyclohexyl or trifluoromethyl;

$R^3$ and $R^4$ independently of one another are hydrogen; —OH; $C_1$–$C_{18}$alkyl; $C_1$–$C_{18}$alkoxy; or halogen or may have one of the definitions of $R^7$;

$R^5$ has one of the definitions given for $R^7$ or is halogen; —O—CO—$R^{12}$; —O—$SO_2$—$R^{13}$ or —O—$R^7$;

$R^6$ is H or $C_1$–$C_{12}$alkyl;

$R^7$ is $C_2$–$C_{18}$alkenyl; or $R^7$ is $C_1$–$C_{12}$alkyl which is substituted by OH, $C_1$–$C_{18}$alkoxy, halogen, —COOH, —COOR$^8$, —CONH$_2$, —CONHR$^9$, —CON(R$^9$)(R$^{10}$), —NH$_2$, —NHR$^9$, —N(R$^9$)(R$^{10}$), —NHCOR$^{11}$, —CN, —OCOR$^{11}$ and/or phenoxy which is unsubstituted or is substituted by $C_1$–$C_{18}$alkyl, $C_1$–$C_{18}$alkoxy or halogen; or $R^7$ is $C_4$–$C_{20}$alkyl which is interrupted by one or more O and substituted by OH or $C_1$–$C_{12}$alkoxy; glycidyl; $C_5$–$C_8$cycloalkyl; cyclohexyl which is substituted by OH, $C_1$–$C_4$alkyl or —OCOR$^{11}$; or $C_7$–$C_{11}$phenylalkyl which is unsubstituted or substituted by OH, Cl or CH$_3$;

$R^8$ is $C_1$–$C_{18}$alkyl; $C_2$–$C_6$hydroxyalkyl; $C_3$–$C_{18}$alkenyl; $C_3$–$C_{20}$alkyl which is interrupted by O, N or S and/or substituted by OH; $C_1$–$C_4$alkyl which is substituted by —P(O)(OR$^{14}$)$_2$, —N(R$^9$)(R$^{10}$) or —OCOR$^{11}$ and/or OH; glycidyl; cyclohexyl or $C_7$–$C_{11}$phenylalkyl;

$R^9$ and $R^{10}$ independently of one another are $C_1$–$C_{12}$alkyl; $C_3$–$C_{12}$alkoxyalkyl; $C_4$–$C_{16}$-dialkylamninoalkyl or $C_5$–$C_{12}$cycloalkyl or $R^9$ and $R^{10}$ together are $C_3$–$C_9$alkylene or -oxaalkylene or -azaalkylene;

$R^{11}$ is $C_1$–$C_{18}$alkyl; $C_2$–$C_{18}$alkenyl or phenyl;

$R^{12}$ is $C_1$–$C_{18}$alkyl; $C_2$–$C_{18}$alkenyl; phenyl; or —R$^{15}$—O—CO—R$^{11}$; or is a group of the formula

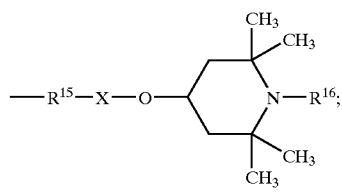

$R^{13}$ is $C_1$–$C_{12}$alkyl; phenyl; naphthyl or $C_7$–$C_{14}$alkylphenyl; and $R^{14}$ is $C_1$–$C_{12}$alkyl or phenyl.

$R^{15}$ is $C_1$–$C_{18}$alkylene or $C_2$–$C_{18}$alkenylene;

$R^{16}$ is hydrogen; $C_1$–$C_8$alkanoyl; $C_1$–$C_{18}$alkyl; $C_1$C$_{18}$alkoxy; $C_5$–$C_8$cycloalkyl; $C_5$–$C_8$cycloalkoxy; $C_7$–$C_{11}$phenylalkyl; $C_7$–$C_{11}$phenylalkyl which is substituted on the phenyl ring by from 1 to 3 radicals $C_1$–$C_4$alkyl or $C_1$–$C_8$alkanoyl; or $C_7$–$C_{11}$phenylalkoxy; and X is a direct bond or —CO—.

Particularly preferred compounds of the formula Ib are those in which $R^1$ and $R^2$ independently of one another are hydrogen or $C_1$–$C_4$alkyl;

$R^3$ and $R^4$ independently of one another are hydrogen; $C_1$–$C_3$alkyl; $C_1$–$C_3$alkoxy or halogen or have one of the definitions of $R^7$ or are OR$^7$;

$R^5$ has one of the definitions given for $R^7$ or is halogen; —O—CO—$R^{12}$ or —O—$R^7$;

$R^6$ is in the o-position to $R^5$ and in the p-position to —OH and is hydrogen, $C_1$–$C_6$alkyl, allyl, $C_6$–$C_{18}$alkanoyl, benzoyl or α-methylbenzyl;

$R^7$ is $C_4$–$C_{18}$alkyl or $C_2$–$C_{18}$alkenyl; or $R^7$ is $C_1$–$C_{12}$alkyl which is substituted by OH, $C_1$–$C_{18}$alkoxy, —COOR$^8$, a group of the formula

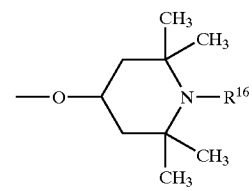

and/or —OCOR$^{11}$; or $R^7$ is $C_7$–$C_{18}$alkyl which is interrupted by from 1 to 6 —O— and substituted by OH; $C_5$–$C_8$cycloalkyl; or $C_7$–$C_{11}$phenylalkyl;

$R^8$ is $C_1$–$C_{18}$alkyl; $C_3$–$C_{18}$alkenyl or a group of the formula

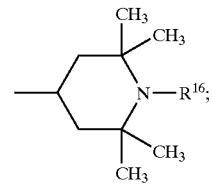

$R^{11}$ is $C_1$–$C_{18}$alkyl or $C_2$–$C_{18}$alkenyl;

$R^{12}$ is $C_1$–$C_{18}$alkyl; $C_2$–$C_{18}$alkenyl; —R$^{15}$—O—CO—CH=CH$_2$; or —R$^{15}$—O—CO—C(CH$_3$)=CH$_2$; or is a group of the formula

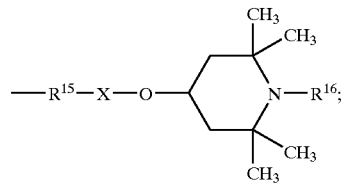

$R^{15}$ is $C_2$–$C_{18}$alkylene; and $R^{16}$ is hydrogen; oxide; $C_2$–$C_8$alkanoyl; $C_1$–$C_{12}$alkyl; hydroxyethyl; $C_1$–$C_{18}$alkoxy; $C_5$–$C_8$cycloalkyl; $C_5$–$C_8$cycloalkoxy; or $C_7$–$C_{11}$phenylalkyl.

Among these, compounds of emphatic significance are those in which $R^1$ and $R^2$ independently of one another are hydrogen or $C_1$–$C_4$alkyl;

$R^3$ and $R^4$ independently of one another are hydrogen or $C_1$–$C_4$alkoxy or $C_1$–$C_4$alkyl;

$R^5$ is —O—$R^7$;

$R^6$ is in the o-position to $R^5$ and in the p-position to OH and is hydrogen or $C_1$–$C_6$alkyl or allyl;

$R^7$ is $C_4$–$C_{18}$alkyl or $C_3$–$C_{18}$alkenyl; or $R^7$ is $C_1$–$C_{12}$alkyl which is substituted by OH, $C_1$–$C_{18}$alkoxy, —COOR$^8$, a group of the formula

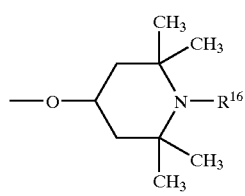

and/or —OCOR$^{11}$;

$R^8$ is $C_1$–$C_{18}$alkyl; and $R^{11}$ is $C_1$–$C_{18}$alkyl or $C_2$–$C_3$alkenyl.

The compounds of the formula I, Ia and Ib can be prepared in correspondence with or in analogy to one of the methods indicated in U.S. Pat. No. 3,442,898, by Friedel-Crafts addition of halopyrimidines onto appropriate phenols.

This is advantageously carried out by reacting one equivalent of a compound of the formula (A)

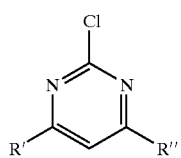

(A)

in which R' and R" independently of one another are each

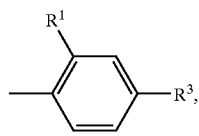

in which $R^1$ is not hydroxyl, with the quantity of equivalents of the corresponding phenol of the formula (B)

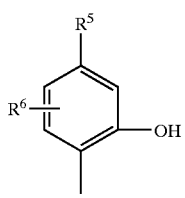

(B)

and, if desired, of the formula (C)

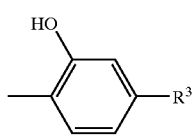

(C)

as there are chlorine atoms in formula (A).

Where different phenols are reacted, the overall reaction is preferably carried out over two or more stages, so that initially one phenol is reacted with the compound of the formula (A), the reaction product is then reacted with another phenol, and the product resulting therefrom is reacted if appropriate with the third phenol. If the end product of the formula I, Ia or Ib is derived, for example, from triresorcinylpyrimidine, then, in accordance with the indications in U.S. Pat. No. 3,442,898, 2,4,6-trichloropyrimidine as the compound of the formula (A) can be reacted in one stage with resorcinol as the compound of the formula (B).

The starting materials are reacted in a manner known per se by reacting them in an inert solvent in the presence of anhydrous AlCl$_3$. Aluminium trichloride and phenol are in this case advantageously employed in excess; for example, aluminium trichloride can be used in a 5–15% molar excess and the phenol in a 1–30%, in particular in a 5–20%, molar excess. Where the compound of the formula (A) contains 1 chlorine atom, 1–1.3 mol, for example, of compound (B) per mole of compound (A) can be employed for the reaction; where the compound of the formula (A) contains 2 or 3 chlorine atoms, then generally the two-fold or three-fold quantity of phenol is used.

Examples of suitable solvents are hydrocarbons, chlorinated hydrocarbons or nitrated aromatic hydrocarbons; high-boiling hydrocarbons are preferred, such as ligroin, toluene or xylene. The temperature is in general not critical; the temperatures usually employed are between 20° C. and the boiling point of the solvent, for example between 50° C. and 150° C. The product can be worked up by common methods, for example by filtration and drying; if required, further purification steps such as recrystallization can be carried out.

Free phenolic hydroxyl groups of the reaction product, especially in the p-position to the pyrimidine ring, can subsequently be etherified or esterified in a known manner; cf. also U.S. Pat. No. 3,442,898. For the preparation of the phenol ethers, the free phenols are preferably reacted with epoxides or halides, especially with glycidyl compounds or appropriate chlorides or bromides.

The starting compounds of the formula (A) are known or can be prepared by known methods or in analogy to the known compounds.

Examples of possible starting compounds are the known amino-aryl-pyrimidines, whose synthesis is described, inter alia, by D. Simon et al., J. Heterocyclic Chem. 22, 1551 (1985).

The exchange of amino on the pyrimidine ring for —OH, and also the exchange of hydroxyl for halogen to form the halopyrimidines, is described in, for example, D. J. Brown and P. Waring, Austr. J. Chem. 26, 443 (1973) and U.S. Pat. No. 3,442,898.

A further method for the preparation of starting compounds of the formula (A) in which at least one of the substituents R' and R" is not —Cl is the reaction of 2,4,6-trichloropyrimidine with a correspondingly substituted phenylmagnesium halide (Grignard reaction). The reaction can likewise be carried out in a known manner, by first reacting a compound of the formula

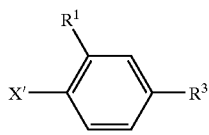

in which X' is Cl or Br with metallic magnesium in an ether, for example in diethyl ether or in tetrahydrofuran (THF), in order to prepare the phenylmagnesium halide. This reagent is then reacted with 2,4,6-trichloropyrimidine to give the compound of the formula (A), preferably with the exclusion of oxygen and moisture. The subsequent work-up can in turn be carried out in a known manner, for example by dilution with an organic solvent, such as toluene, hydrolysis of the residual phenylmagnesium halide with aqueous HCl, and separation, drying and concentration of the organic phase.

Some of the compounds obtained of the formula (A) are new compounds which are likewise a subject of the invention. These are compounds of the formula (A')

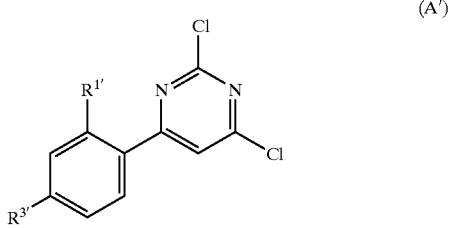

(A')

in which $R^1$ is H; $C_1$–$C_{12}$alkyl; cyclohexyl or trifluoromethyl; and $R^{3'}$ is $C_1$–$C_{18}$alkyl; $C_1$–$C_{18}$alkoxy; $C_2$–$C_{18}$alkenyl; halogen; $C_3$–$C_{18}$alkoxy which is interrupted by —O—; or cyclohexyl. Among these, those compounds of formula (A') are preferred in which $R^{1'}$ is hydrogen or $C_1$–$C_4$alkyl and $R^{3'}$ is $C_1$–$C_{18}$alkyl or $C_1$–$C_{18}$ alkoxy or Cl, for example $C_1$–$C_4$alkyl or $C_1$–$C_4$alkoxy or Cl, especially methyl, methoxy or Cl.

The compounds of the formula Ib according to the invention can be used as stabilizers for organic materials against damage by light, oxygen or heat. The compounds according to the invention are especially suitable as light stabilizers.

Examples of the materials to be stabilized are oils, fats, waxes, cosmetics, biocides or photographic materials. A utility of particular interest is in polymeric materials, for example in plastics, rubbers, paints or adhesives. Examples of polymers and other substrates which can be stabilized in this way are the following:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly(α-methylstyrene).

6. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene styrene.

7. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated or sulfochlorinated polyethylene, copolymers of ethylene and chlorinated ethylene, epi-chlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from $\alpha,\beta$-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer, polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, polyisocyanates or epoxy resins.

26. Crosslinked epoxy resins derived from polyepoxides, for example from bisglycidyl ethers or from cycloaliphatic diepoxides.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.

The invention therefore also relates to a composition comprising

A) an organic material which is sensitive to damage by light, oxygen and/or heat, and B) as stabilizer, a compound of the formula Ib.

The compounds of the formula Ib according to the invention can be employed with particular advantage in compositions which contain as component A a synthetic organic polymer, especially a thermoplastic polymer or a photographic material. Examples of suitable thermoplastic polymers are polyolefins and polymers which contain heteroatoms in the principal chain. Preferred compositions are those in which component A is a photographic material or a thermoplastic polymer which contains nitrogen, oxygen and/or sulfur, especially nitrogen or oxygen, in the principal chain.

Polymers which contain heteroatoms in the principal chain are in particular polymers containing O, S and/or N. Examples of such polymers are the following classes of thermoplastic polymers:

1. Polyacetals, such as polyoxymethylene, and those polyoxymethylenes which contain comonomers such as, for example, ethylene oxide; polyacetals which are modified with thermoplastic polyurethanes, acrylates or MBS.

2. Polyphenylene oxides and polyphenylene sulfides and mixtures thereof with styrene polymers or polyamides.

3. Polyamides and copolyamides, for example those derived from diamines and dicarboxylic acids and/or from aminocarboxylic acids or the corresponding lactones, such as polyamide 4, polyamide 6, polyamide 6/6, 6/10, 6/9, 6/12, 4/6, polyamide 11, polyamide 12, aromatic polyamides based on m-xylene, diamine and adipic acid; polyamides prepared from hexamethylenediamine and iso- and/or terephthalic acid and, if desired, an elastomer as modifier, for example poly-2,4,4-trimethylhexamethyleneterephthalamide, poly-m-phenyleneisophthalamide; block copolymers of the above-mentioned polyamides with polyolefins, olefin copolymers, ionomers or chemically bonded or grafted elastomers; or with polyethers, for example with polyethylene glycol, polypropylene glycol or polytetramethylene glycol; additionally, polyamides or copolyamides modified with EPDM or ABS; and polyamides condensed during processing (RIM polyamide systems).

4. Polyureas, polyimides, polyamide-imides and polybenzimidazoles.

5. Polyesters, for example those derived from dicarboxylic acids and dialcohols and/or from hydroxycarboxylic acids or the corresponding lactones, such as polyethylene terephthalate, polybutylene terephthalate, poly-1,4-dimethylolcyclohexane terephthalate, polyhydroxybenzoates, and block polyether-esters derived from polyethers having terminal hydroxyl groups; also, polyesters modified with polycarbonates or MBS.

6. Polycarbonates and polyester carbonates, especially aromatic polycarbonates such as those based on 2,2-bis(4-hydroxyphenyl)propane or 1,1-bis(4-hydroxyphenyl) cyclohexane.

7. Polysulfones, polyether sulfones and polyether ketones, especially aromatic polymers from this class.

8. Mixtures (polyblends) of these polymers with one another or with other polymers, for example with polyolefins, polyacrylates, polydienes or other elastomers as impact modifiers.

Preferred among these are the polycarbonates, polyesters, polyamides, polyacetals, polyphenylene oxides and polyphenylene sulfides, but especially the polycarbonates. This should be understood as referring in particular to those polymers whose constitutional repeating unit is of the formula

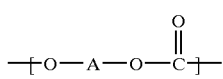

in which A is a divalent phenolic radical. Examples of A are given, inter alia, in U.S. Pat. No. 4,960,863 and DE-A-3 922 496. A may, for example be derived from hydroquinone, resorcinol, from dihydroxybiphenyls or bisphenols in the broadest sense such as bis(hydroxyphenyl)alkanes, bis (hydroxyphenyl)cycloalkanes, bis(hydroxyphenyl)sulfides, bis(hydroxyphenyl)ethers, bis(hydroxyphenyl)ketones, bis (hydroxyphenyl)sulfones, bis(hydroxyphenyl)sulfoxides, α,α'-bis(hydroxyphenyl)diisopropylbenzenes, for example from the compounds 2,2-bis(4-hydroxyphenyl)propane, 2,2-bis(3,5-dimethyl-4-hydroxyphenyl)propane, 2,2-bis(3,5-dichloro-4-hydroxyphenyl)propane, 2,2-bis(3,5-dibromo-4-hydroxyphenyl)propane, 1,1-bis(4-hydroxyphenyl) cyclohexane or from the compounds of the formulae

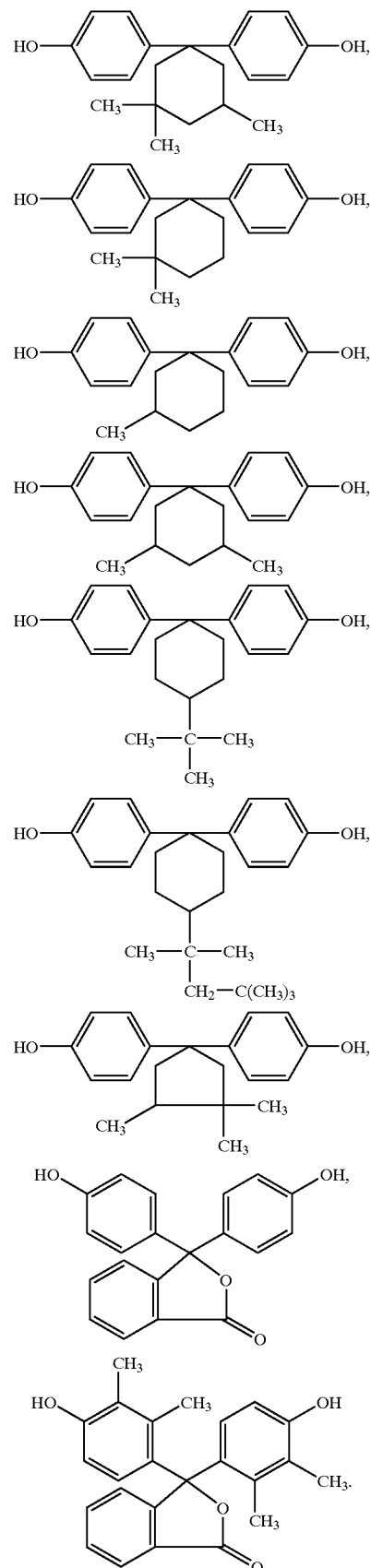

Other compositions of interest are those in which component (A) is a polyolefin, for example polyethylene or polypropylene.

The invention also relates to a method of stabilizing organic material against damage by light, oxygen and/or heat, which comprises adding to this material a compound of the formula Ib as stabilizer, and to the use of compounds of the formula Ib for stabilizing organic material.

The quantity of stabilizer to be used depends on the organic material to be stabilized and on the intended use of the stabilized material. In general, the composition according to the invention contains from 0.01 to 15, in particular from 0.05 to 10 and especially from 0.1 to 5 parts by weight of the stabilizer (component B) per 100 parts by weight of component A.

Incorporation into the organic polymers, for example into the synthetic organic and, in particular, thermoplastic polymers can be effected by adding the compounds according to the invention and, if desired, other additives by the methods conventional in industry. Incorporation can be effected advantageously before or during shaping, for example by mixing the pulverulent components or by adding the stabilizer to the melt or solution of the polymer, or by applying the dissolved or dispersed compounds to the polymer, followed if desired by the evaporation of the solvent. In the case of elastomers, these may also be stabilized as latices. A further possibility for incorporating the compounds according to the invention into polymers consists in their addition before or during the polymerization of the corresponding monomers or before crosslinking.

The compounds according to the invention or mixtures thereof can also be added to the plastics to be stabilized in the form of a masterbatch which contains these compounds in, for example, a concentration of from 2.5 to 25% by weight.

The compounds according to the invention are advantageously incorporated by the following possible methods:
- as emulsion or dispersion (e.g. to latices or emulsion polymers)
- as a dry mixture during the mixing of additional components or polymer mixtures
- by direct addition to the processing apparatus (e.g. extruder, internal mixer etc.)
- as solution or melt.

The resulting stabilized polymer compositions can be converted, by the conventional methods such as hot pressing, spinning, extrusion or injection moulding, into shaped articles such as fibres, films, strips, plates, webbed plates, vessels, pipes and other profiles.

The invention therefore also relates to the use of the polymer composition according to the invention for the production of a shaped article.

The utility of the compositions in multilayer systems is also of interest. In this case a polymer composition according to the invention having a relatively high content of stabilizer of the formula Ib, for example 5–15% by weight, is applied in a thin layer (10–100 μm) to a shaped article made from a polymer which contains little or no stabilizer of the formula Ib. Application can be carried out simultaneously with the shaping of the basic structure, for example by so-called coextrusion. The composition can also be applied, however, to the ready-formed basic structure, for example by lamination with a film or by coating with a solution. The external layer of layers of the finished article have the function of a UV filter which protects the interior or the article inside against UV light. The external layer preferably contains 5–15% by weight, in particular 5–10% by weight, of at least one stabilizer of the formula Ib.

The use of the polymer composition according to the invention for the production of multilayer systems, where the external layer(s) comprise a polymer composition according to the invention in a thickness of 10–100 μm whereas the inner layer contains little or no stabilizer of the formula Ib, is therefore a further subject of the invention.

The use of a polymer composition according to the invention in which component A is a polycarbonate for the production of multilayer systems is of particular interest.

The polymers stabilized in this way are distinguished by high resistance to weathering and especially by high resistance to UV light. By this means they show long-term retention, even when used outdoors, of their mechanical properties and their colour and gloss.

The stabilizer (component B) may also be a mixture of two or more compounds according to the invention. The organic materials, stabilized coating compositions or compositions according to the invention may also contain, in addition to the stabilizer of the formula I, Ia or Ib, other stabilizers or other additives, for example antioxidants, further light stabilizers, metal deactivators, phosphites or phosphonites. Examples of these are the following stabilizers:

1. Antioxidants
  1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)4,6-dimethylphenol, 2,6-dioctadecyl-4-methylphenol, 2,4,6-tricyclohexylphenol, 2,6-di-tert-butyl-4-methoxymethylphenol, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.
  1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.
  1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl)adipate.
  1.4. Tocopherols, for example α-tocopherol, β-tocopherol, γ-tocopherol, δ-tocopherol and mixtures thereof (Vitamin E).
  1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thio-bis(6-tert-butyl-2-methylphenol), 4,4'-thiobis-(3,6-di-sec-amylphenol), 4,4'-bis-(2,6-dimethyl-4-hydroxyphenyl)disulfide.
  1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylene-bis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'- methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy2-methylphenyl) pentane.

1.7. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tris-(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5di-tert-butyl-4-hydroxybenzylmercaptoacetate.

1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis-[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine Compounds, for example 2,4-bis (octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris-(3,5-di-tert-butyl-4-hydroxybenzyl) isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2] octane.

1.14. Esters of β-(5-tert-butyl-4-hydroxy-3-methylphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2] octane.

1.15. Esters of β-(3,5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2] octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis-(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2] octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamine, N,N'-bis(3,5-di-tert-butyl-4-hydroxyphenylpropionyl) trimethylenediamine, N,N'-bis(3,5-di-tert-butyl-4-hydroxyphenylpropionyl)hydrazine.

2. UV absorbers and light stabilisers 2.1. 2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis-(α,α-dimethylbenzyl)-2'-hydroxyphenyl)benzotriazole, mixture of 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)carbonylethyl]-2'-hydroxyphenyl)-5chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyl-oxycarbonylethyl)phenyl) benzotriazole, 2-(3'-tert-butyl-5'-[2-(2-ethylhexyloxy) carbonyl-ethyl]-2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxy-carbonylethyl)phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO(CH$_2$)$_3$]$_2$, where R=3'-tert-butyl-4'-hydroxy-5'-2H-benzotriazol-2-ylphenyl.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutylphenyl salicylate, phenyl salicylate, octylphenyl salicylate, dibenzoyl resorcinol, bis(4-tert-butylbenzoyl) resorcinol, benzoyl resorcinol, 2,4-di-tertbutylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxy-cinnamate, butyl α-cyano-β-methyl-p-methoxy-cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoxnimes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-piperidyl)sebacate, bis(2,2,6,6-tetramethyl-piperidyl)succinate, bis(1,2,2,6,6-pentamethylpiperidyl)sebacate, bis(1,2,2,6,6-pentamethylpiperidyl)n-butyl-3,5-di-tert-butyl-4-hydroxybenzylmalonate, the condensate of 1-(2-hydroxyethyl)-2,2,6,6-tetramethyl-4-hydroxypiperidine and succinic acid, the condensate of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl)nitrilotriacetate, tetrakis(2,2,6,6-tetramethyl-4-piperidyl)-1,2,3,4-butane-tetracarboxylate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazasprio[4.5]decan-2,4-dion, bis(1-octyloxy-2,2,6,6-tetramethylpiperidyl)sebacate, bis(1-octyloxy-2,2,6,6-tetramethylpiperidyl)succinate, the condensate of N,N'-bis-(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl)pyrrolidine-2,5-dione.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide and mixtures of ortho- and para-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2hydroxy-3-butyloxy-propoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphsophite, tristearyl sorbitol triphosphite, tetrakis(2,4-di-tert-butylphenyl)4,4'-biphenylene diphosphonite, 6-isooctyloxy-2,4,8,10-tetra-tert-butyl-12H-dibenz[d,g]-1,3,2-dioxaphosphocin, 6-fluoro-2,4,8,10-tetra-tert-butyl-12-methyl-dibenz[d,g]-1,3,2-dioxaphosphocin, bis(2,4-di-tert-butyl-6-methylphenyl)methylphosphite, bis(2,4-di-tert-butyl-6methylphenyl)ethylphosphite.

5. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. Polyamide stabilisers, for example, copper salts in combination with iodides and/or phosphorus compounds and salts of divalent manganese.

7. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or tin pyrocatecholate.

8. Nucleating agents, for example, 4-tert-butylbenzoic acid, adipic acid, diphenylacetic acid.

9. Fillers and reinforcing agents, for example, calcium carbonate, silicates, glass fibres, asbestos, talc, kaolin, mica, barium sulfate, metal oxides and hydroxides, carbon black, graphite.

10. Other additives, for example, plasticisers, lubricants, emulsifiers, pigments, optical brighteners, flameproofing agents, antistatic agents and blowing agents.

11. Benzofuranones and indolinones, for example those disclosed in U.S. Pat. Nos. 4,325,863, 4,338,244, 5,175,312, 5,216,052, 5,252,643, DE-A-4 316 611, DE-A4 316 622, DE-A-4 316 876, EP-A-0 589 839 or EP-A-0 591 102 or 3-[4-(2-acetoxyethoxy)phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl) benzofuran-2-one], 5,7-di-tert-butyl-3-(4-ethoxyphenyl) benzofuran-2-one, 3-(4-acetoxy-3,5-dimethylphenyl)-5,7-di-tert-butyl-benzofuran-2-one, 3-(3,5-dimethyl-4-pivaloyloxyphenyl) -5,7-di-tert-butyl-benzofuran-2-one.

The nature and quantity of the further stabilizers added depends on the nature of the substrate to be stabilized and on its intended use; in many cases from 0.1 to 5% by weight is used, based on the polymer to be stabilized.

A further subject of the present invention is the use of a compound of the formula Ib in photographic materials as a stabilizer against damage by light, especially damage by UV light, and the photographic material comprising a compound of the formula Ib, with mixtures of compounds of the formula Ib also being relevant.

The compounds according to the invention can be used for all types of photosensitive material. They can be employed, for example, for colour paper, colour reversal paper, direct positive colour material, colour negative film, colour positive film, colour reversal film and others. They are preferably used inter alia for photosensitive colour material which contains a reversal substrate or which forms positives.

The compounds according to the invention can also be combined with other UV absorbers, especially those which are dispersible in aqueous gelatin, for example with hydroxyphenylbenzotriazoles (cf. for example U.S. Pat. Nos. 4,853,471, 4,973,702, 4,921,966 and 4,973,701), benzophenones, oxanilides, cyanoacrylates, salicylic esters, acrylonitriles or thiazolines. It is advantageous here for these other UV absorbers dissolved in oil to be employed in different layers of the photographic material than the UV absorbers according to the invention. Photographic materials which can be stabilized with particularly good success are materials similar to those described in U.S. Pat. No. 4,518,686.

The present application therefore relates to photographic material comprising, on a support, a blue-sensitive, a green-sensitive and/or a red-sensitive silver halide emulsion layer and, if desired, a protective layer, with a layer containing a UV absorber being arranged above the topmost silver halide emulsion layer, which UV absorber is of the formula Ib.

In a further embodiment, the material according to the invention comprises a layer containing a UV absorber of the formula Ib which is arranged between the green-sensitive and the red-sensitive silver halide emulsion layer, a further layer containing a UV absorber of the formula Ib being able to be arranged above the topmost silver halide emulsion layer.

Good results are also obtained if the UV absorber of the formula Ib is additionally contained in the red-sensitive silver halide emulsion layer.

Other preferred photographic materials are those which have a layer comprising a compound of the formula Ib above the topmost silver halide emulsion layer and/or between the green-sensitive and the red-sensitive silver halide emulsion layer, an oil-soluble UV absorber additionally being contained in a layer which contains no UV absorber of the formula Ib.

Furthermore, it may be advantageous for all or some of the said layers which can contain a UV absorber to contain a UV absorber of the formula Ib and/or a further UV absorber which is dispersible in aqueous gelatin, but where it is necessary for a UV absorber of the formula Ib to be contained in at least one layer. The material according to the invention preferably contains gelatin interlayers between the silver halide emulsion layers.

Preferred photographic materials of this kind are those in which the silver halide in the blue-sensitive, green-sensitive and/or red-sensitive layer is silver chloride bromide, at least 90 mol % of which consists of silver chloride.

Further preferred photographic materials are those which contain the silver halide emulsion layers in the sequence blue-sensitive, green-sensitive and red-sensitive silver halide emulsion layer.

In relation to materials containing benzotriazole UV absorbers, the photographic materials according to the invention offer the advantage that the UV absorbers of the formula Ib are required in a comparatively small quantity to give sufficient protection against UV radiation. This means that the thickness of the layers in which the UV absorbers of the formula Ib are incorporated can be very thin, which has a positive effect on, for example, the distinctness of the images produced using this material.

Yellow couplers which can be used in the material according to the invention are preferably compounds of the formula A

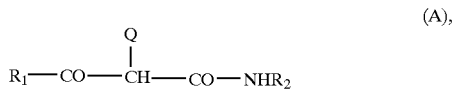

(A), in which $R_1$ is alkyl or aryl, $R_2$ is aryl and Q is hydrogen or a group which can be detached by reaction with the oxidized developer.

One group of yellow couplers are those compounds of the formula A in which $R_1$ is t-butyl and $R_2$ is a group of the formula

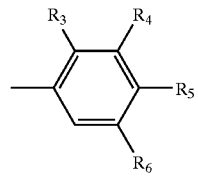

in which $R_3$ is hydrogen, halogen, alkyl or alkoxy and $R_4$, $R_5$ and $R_6$ are hydrogen, halogen, alkyl, alkenyl, alkoxy, aryl, carboxyl, alkoxycarbonyl, a carbamoyl group, a sulfone or sulfamoyl group, an alkylsulfonamido group, acylamino group, ureido group or amino group.

Preferably, $R_3$ is chlorine, $R_4$ and $R_5$ are hydrogen and $R_6$ is an acrylamino group. This also includes the compounds of the formula

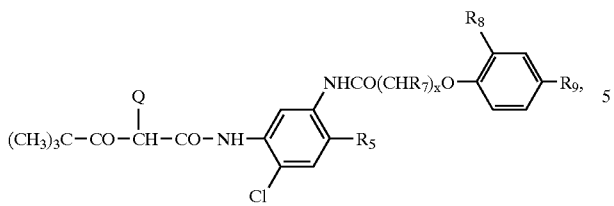

in which x is 0–4, $R_7$ is hydrogen or alkyl and $R_8$ and $R_9$ are alkyl.

Another group of yellow couplers is of the formula B

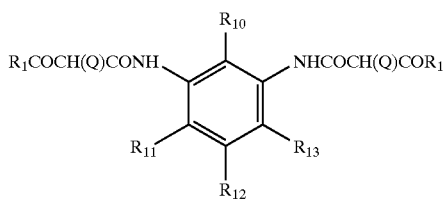

(B), in which $R_{10}$ is hydrogen, halogen or alkoxy, $R_{11}$, $R_{12}$ and $R_{13}$ are hydrogen, halogen, alkyl, alkenyl, alkoxy, aryl, carboxyl, alkoxycarbonyl, a carbamoyl group, a sulfone group, sulfamoyl group, sulfonamido group, acylamino group, ureido group or amino group and $R_1$ and Q are as defined above.

This includes compounds of the formula B in which $R_1$ is t-butyl, $R_{10}$ is chlorine, $R_{11}$ and $R_{13}$ are hydrogen and $R_{12}$ is alkoxycarbonyl.

In the compounds of the formula A and B the leaving group Q can be hydrogen or it is a heterocyclic group

in which $R_{14}$ is a divalent organic group which completes the ring to give a 4–7-membered ring, or Q is a group —$OR_{15}$ in which $R_{15}$ is alkyl, aryl, acyl or a heterocyclic radical.

The yellow couplers are conventionally used in a quantity of 0.05–2 mol and preferably 0.1–1 mol per mole of silver halide.

Examples of magenta couplers are simple 1-aryl-5-pyrazolones or pyrazole derivatives fused with 5-membered hetero rings, for example imidazopyrazoles, pyrazolopyrazoles, pyrazolotriazoles or pyrazolotetrazoles.

One group of magenta couplers comprises 5-pyrazolones of the formula C

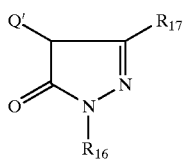

(C), as described in British Patent 2 003 473. In this formula $R_{16}$ is hydrogen, alkyl, aryl, alkenyl or a heterocyclic group. $R_{17}$ is hydrogen, alkyl, aryl, a heterocyclic group, an ester group, alkoxy group, alkylthio group, carboxyl group, arylamino group, acylamino group, (thio)urea group, (thio)carbamoyl group, guanidino group or sulfonamido group. $R_{17}$ is preferably a group

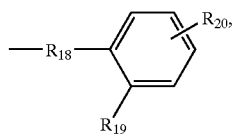

in which $R_{18}$ is imino, acylamino or ureido, $R_{19}$ is hydrogen, halogen, alkyl or alkoxy, $R_{20}$ is hydrogen, alkyl, acylamino, carbamoyl, sulfamoyl, sulfonamido, alkoxycarbonyl, acyloxy or a urethane group.

If Q' is hydrogen, then the magenta coupler is tetraequivalent with respect to the silver halide.

Typical examples of this type of magenta coupler are compounds of the formula

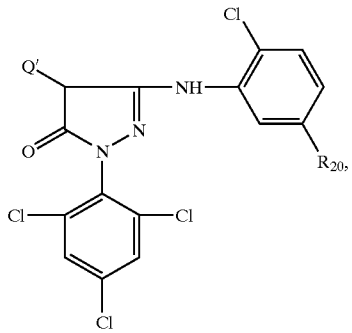

in which $R_{20}$ is as defined above and Q', as described above, is a leaving group. These compounds are preferably in the material according to the invention.

Further examples of such tetraequivalent magenta couplers can be found in U.S. Pat. Nos. 2,983,608, 3,061,432, 3,062,653, 3,127,269, 3,152,896, 3,311,476, 3,419,391, 3,519,429, 3,558,319, 3,582,322, 3,615,506, 3,684,514, 3,834,908, 3,888,680, 3,891,445, 3,907,571, 3,928,044, 3,930,861, 3,930,866 and 3,933,500 and in JP-A-89/309 058.

If Q' in formula C is not hydrogen but a group which is eliminated during the reaction with the oxidized developer, then the magenta coupler is diequivalent. Q may in this case be, for example, halogen or a group which is attached to the pyrazole ring via O, S or N. Such diequivalent couplers give a higher colour density and are more reactive with respect to the oxidized developer than the corresponding tetraequivalent magenta couplers.

Examples of diequivalent magenta couplers are described in U.S. Pat. Nos. 3,006,579, 3,419,391, 3,311,476, 3,432, 521, 3,214,437, 4,032,346, 3,701,783, 4,351,897, 3,227,554, in EP-A-133 503, DE-A-2 944 601, JP-A-78/34 044, 74/53 435, 74/53 436, 75/53 372 and 75/122 935.

2 pyrazolone rings can be linked via a divalent Q', to give so-called bis couplers. Examples of these are described in U.S. Pat. Nos. 2,632,702, 2,618,864, GB-A-968 461, GB-A-786 859, JP-A-76/37 646, 59/4 086, 69/16 110, 69/26 589, 74/37 854 and 74/29 638. Y is preferably an O-alkoxyarylthio group.

As mentioned above, pyrazoles fused with 5-membered heterocycles—so-called pyrazoloazoles—can also be used as magenta couplers. Their advantages over simple pyrazoles are that they possess colours with greater resistance to formalin and purer absorption spectra.

Magenta couplers of the pyrazoloazole type, which are likewise preferred, may be represented by the formula

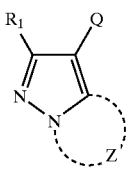

(M-7)

in which $R_1$ is hydrogen or a substituent, Z represents the non-metallic atoms necessary to complete a 5-membered ring containing 2 or 3 nitrogen atoms, which ring may be substituted, and Q is hydrogen or a leaving group.

Among these, preferred magenta couplers are those of the formulae

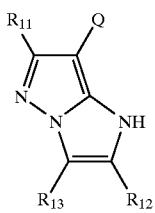

(M-8)

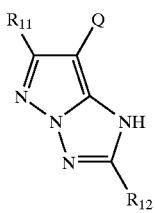

(M-9)

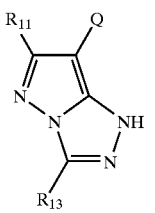

(M-10)

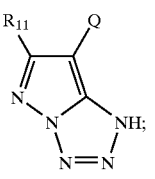

(M-11)

$R_{11}$, $R_{12}$ and $R_{13}$ independently of one another are, for example, hydrogen, halogen, a group of the formula —$CR_3$ in which the radicals R independently of one another are hydrogen or alkyl, aryl, heterocyclyl, cyano, hydroxyl, nitro, carboxyl, amino, alkoxy, aryloxy, acylamino, alkylamino, anilino, ureido, sulfamoylamino, alkylthio, arylthio, alkoxycarbonylamino, sulfonamido, carbamoyl, sulfamoyl, sulfonyl, alkoxycarbonyl, heterocyclyloxy, azo, acyloxy, carbamoyloxy, silyloxy, aryloxycarbonylamino, imido, heterocyclyl-thio, sulfinyl, phosphonyl, aryloxycarbonyl, acyl or azolyl, and preferably hydrogen; halogen (e.g. chlorine, bromine), a group of the formula —$CR_3$ in which the radicals R independently of one another are hydrogen or alkyl, aralkyl, alkenyl, alkynyl, cycloalkyl or cycloalkenyl and particularly preferably methyl, ethyl, propyl, isopropyl, t-butyl, tridecyl, 2-methanesulfonylethyl, 3-(3-pentadecylphenoxy)propyl, 3-(4-(2-(4-(4-hydroxyphenylsulfonyl)phenoxy)dodecanamido)phenyl) propyl, 2-ethoxytridecyl, trifluoromethyl, cyclopentyl, 3-(2, 4-di-t-amylphenoxy)propyl); aryl (e.g. phenyl, 4-t-butylphenyl, 2,4-di-t-amylphenyl, 4-tetradecaneamidophenyl); heterocyclyl (e.g. 2-furyl, 2-thienyl, 2-pyrimidyl, 2-benzothiazolyl); cyano; hydroxyl, nitro; carboxyl; amino; alkoxy (e.g. methoxy, ethoxy, 2-methoxyethoxy; 2-dodecylethoxy, 2-methanesulfonylethoxy); aryloxy (e.g. phenoxy, 2-methylphenoxy, 4-t-butylphenoxy, 3-nitrophenoxy, 3-t-butyloxycarbamoylphenoxy, 3-methoxycarbamoyl); acylamino (e.g. acetoamido, benzamido, tetradecanamido, 2-(2, 4-di-t-amylphenoxy)butanamido, 4-(3-t-butyl-4hydroxyphenoxy)butanamido, 2-(4-(4-hydroxyphenylsulfonyl)phenoxy)decanamido); methylbutylamino); anilino (e.g. phenylamino, 2-chloroanilino, 2-chloro-5-tetradecanaminoanilino, 2-chloro-5-dodecyloxycarbonylanilino, N-acetylanilino, 2-chloro-5-(alpha-(3-t-butyl-4-hydroxyphenoxy) dodecanamidoanilino); ureido (e.g. phenylureido, methylureido, N,N-dibutylureido); sulfamoylamino (e.g. N,N-dipropylsulfamoylamino, N-methyl-N-decylsulfamoylamino); alkylthio (e.g. methylthio, octylthio, tetradecylthio, 2-phenoxyethylthio, 3-phenoxypropylthio, 3-(4-t-butylphenoxy)propylthio); arylthio (e.g. phenylthio, 2-butoxy-5-t-octylphenylthio, 3-pentadecylphenylthio, 2-carboxyphenylthio, 4-tetradecanamidophenylthio); alkoxycarbonylamino (e.g. methoxycarbonylamino, tetradecyloxycarbonylamino); sulfonamido (e.g. methanesulfonamido, hexadecanesulfonamido, benzenesulfonamido, p-toluenesulfonamido, octadecanesulfonamido, 2-methyloxy-5-t-butylbenzenesulfonamido); carbamoyl (e.g. N-ethylcarbamoyl, N,N-dibutylcarbamoyl, N-(2-dodecyloxyethyl)-carbamoyl, N-methyl-N-dodecylcarbamoyl, N-(3-(2,4-di-t-amylphenoxy)propyl)-carbamoyl); sulfamoyl (e.g. N-ethylsulfamoyl, N,N-dipropylsulfamoyl, N-(2-dodecyloxyethyl)sulfamoyl, N-ethyl-N-dodecylsulfamoyl, N,N-diethylsulfamoyl); sulfonyl (e.g. methanesulfonyl, octanesulfonyl, benzenesulfonyl, toluenesulfonyl); alkoxycarbonyl (e.g. methoxycarbonyl, butoxycarbonyl, dodecyloxycarbonyl, octadecyloxycarbonyl); heterocyclyl-oxy (e.g. 1-phenyltetrazolyl-5-oxy, 2-tetrahydropyranyloxy); azo (e.g. phenylazo, 4-methoxyphenylazo, 4-pivaloylaminophenylazo, 2-hydroxy-4-propanoylphenylazo); acyloxy (e.g. acetoxy); carbamoyloxy (e.g. N-methylcarbamoyloxy, N-phenylcarbamoyloxy); silyloxy (e.g. trimethylsilyloxy, dibutylmethylsilyloxy); aryloxycarbonylamino (e.g. phenoxycarbonylamino); imido (e.g. N-succinimido, N-phthalimido, 3-octadecenylsuccinimido); heterocyclyl-thio (e.g. 2-benzothiazolylthio, 2,4-diphenyloxy-1,3,5-triazole-6-thio, 2-pyridylthio); sulfinyl (e.g. dodecanesulfinyl, 3-pentadecylphenylsulfinyl, 3-phenoxypropylsulfonyl); phosphonyl (e.g. phenoxy-phosphonyl octyloxyphosphonyl, phenylphosphonyl); aryloxycarbonyl (e.g. phenoxycarbonyl); acyl (e.g. acetyl, 3-phenylpropanoyl, benzoyl, 4-dodecyloxybenzoyl); azolyl (e.g. imidazolyl, pyrazolyl, 3-chloropyrazol-1-yl).

These substituents may if desired be substituted further, for example by halogen or by an organic radical which is attached via a C, O, N or S atom.

The preferred groups $R_{11}$ are alkyl, aryl, alkoxy, aryloxy, alkylthio, ureido, urethane and acylamino groups.

$R_{12}$ can be as defined for $R^{11}$ and is preferably hydrogen, alkyl, aryl, a heterocyclic ring, alkoxycarbonyl, carbamoyl, sulfamoyl, sulfinyl, acyl or cyano.

$R_{13}$ can be as defined for $R_{11}$ and is preferably hydrogen, alkyl, aryl, heterocyclyl, alkoxy, aryloxy, alkylthio, arylthio, alkoxycarbonyl, carbamoyl or acyl, preferably alkyl, aryl, heterocyclyl, alkylthio or arylthio.

Q is hydrogen or a leaving group such as halogen, alkoxy, aryloxy, acyloxy, alkyl- or arylsulfonyloxy, acylamino, alkyl- or arylsulfonamido, alkoxycarbonyloxy, aryloxycarbonyloxy, alkyl, aryl- or heterocyclyl-S-carbamoylamino, a 5-membered or 6-membered nitrogen-containing heterocyclic radical, imido and arylazo. These groups may if desired be further substituted as indicated for $R_{11}$.

Q is preferably halogen (e.g. fluorine, chlorine, bromine); alkoxy (e.g. ethoxy, dodecyloxy, methoxyethylcarbamoylmethoxy, carboxypropyloxy, methanesulfonylethoxy, ethoxycarbonylmethoxy); aryloxy (e.g. 4-methylphenoxy, 4-chlorophenoxy, 4-methoxyphenoxy, 4-carboxyphenoxy, 3-ethoxycarboxyphenoxy, 3-acetylaminophenoxy, 2-carboxyphenoxy); acyloxy (e.g. acetoxy, tetradecanoyloxy, benzoyloxy); alkyl- or arylsulfonyloxy (e.g. methanesulfonyloxy, toluenesulfonyloxy); acylamino (e.g. dichloroacetylamino, heptafluorobutyrylamino); alkyl- or arylsulfonamido (e.g. methanesulfonamido, trifluoromethanesulfonamido, p-toluenesulfonylamido); alkoxycarbonyloxy (e.g. ethoxycarbonyloxy, benzyloxycarbonyloxy); aryloxycarbonyloxy (e.g. phenoxycarbonyloxy); alkyl-, aryl- or heterocyclyl-S-(e.g. dodecylthio, 1-carboxydodecylthio, phenylthio, 2-butoxy-5-t-octylphenylthio, tetrazolylthio); carbamoylamino (e.g. N-methylcarbamoylamino, N-phenylcarbamoylamino); 5-membered or 6-membered nitrogen-containing ring (e.g. imidazolyl, pyrazolyl, triazolyl, tetrazolyl, 1,2-dihydro-2-oxo-1-pyridyl); imido (e.g. succinimido, hydantoinyl); arylazo (e.g. phenylazo, 4-methoxyphenylazo).

Q can also form corresponding bis compounds by condensation of 4 equivalents of coupler with an aldehyde or ketone. Q may also contain photographically active groups such as development inhibitors or development accelerators. Q is preferably halogen, alkoxy, aryloxy, alkylthio, arylthio or a 5-membered or 6-membered nitrogen-containing heterocyclic group which is attached to the coupling site via a nitrogen atom.

Pyrazolotetrazoles are described in JP-A-85/33 552; pyrazolo-pyrazoles in JP-A-85/43 695; pyrazolo-imidazoles in JP-A-85/35 732, JP-A-86/18 949 and U.S. Pat. No. 4,500,630; pyrazolo-triazoles in JP-A-85/186 567, JP-A-86/47 957, JP-A-85/215 687, JP-A-85/197 688, JP-A-85/172 982, EP-A-119 860, EP-A-173 256, EP-A-178 789, EP-A-178 788 and in Research Disclosure 84/24 624.

Other pyrazoloazole magenta couplers are described in: JP-A-86/28 947, JP-A-85/140 241, JP-A-85/262 160, JP-A-85/213 937, JP-A-87/278 552, JP-A-87/279 340, JP-A-88/100 457, EP-A-177 765, EP-A-176 804, EP-A-170 164, EP-A-164 130, EP-A-178 794, DE-A-3 516 996, DE-A-3 508 766 and Research Disclosure 81/20 919, 84/24 531 and 85/25 758.

Cyan couplers may for example be derivatives of phenol, of 1-naphthol or of pyrazoloquinazolone. Structures of the formula E are preferred

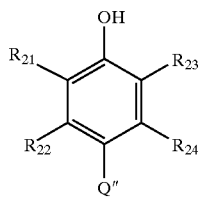

in which $R_{21}$, $R_{22}$, $R_{23}$ and $R_{24}$ are hydrogen, halogen, alkyl, carbamoyl, amino, sulfonamido, phosphoramido or ureido. $R_{21}$ is preferably H or Cl, and $R_{22}$ is preferably an alkyl or amino group. $R_{23}$ is preferably an amino group and $R_{24}$ is preferably hydrogen. Q" is hydrogen or a leaving group which is detached during the reaction with the oxidized developer. A detailed list of cyan couplers can be found in U.S. Pat. No. 4,456,681.

Other examples of cyan couplers can be found in the following US-A documents: U.S. Pat. Nos. 2,369,929, 2,423,730, 2,434,272, 2,474,293, 2,521,293, 2,521,908, 2,698,794, 2,706,684, 2,772,162, 2,801,171, 2,895,826, 2,908,573, 3,034,892, 3,046,129, 3,227,550, 3,253,294, 3,311,476, 3,386,301, 3,419,390, 3,458,315, 3,476,560, 3,476,563, 3,516,831, 3,560,212, 3,582,322, 3,583,971, 3,591,383, 3,619,196, 3,632,347, 3,652,286, 3,737,326, 3,758,308, 3,839,044, 3,880,661, 4,004,929, 4,124,396, 4,333,999, 4,463,086, 4,456,681, 4,873,183 and 4,923,791 and in EP-A-354 549 and EP-A-398 664.

The cyan couplers preferably employed in the red-sensitive silver halide emulsion layer of the material according to the invention are those of the formula

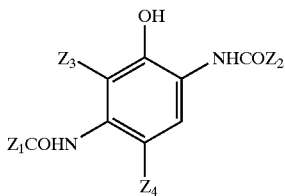

and/or of the formula

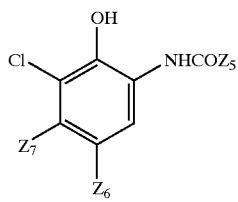

in which
$Z_1$ is alkyl or aryl, $Z_2$ is alkyl, cycloalkyl, aryl, a heterocyclic group or a ballast group, $Z_3$ is hydrogen or halogen, $Z_1$ and $Z_3$ together may form a ring, and $Z_4$ is hydrogen or a leaving group, and $Z_5$ is a ballast group, $Z_6$ is hydrogen or a leaving group and $Z_7$ is alkyl.

The colour developers conventionally used for colour-photographic materials are p-dialkylaminoanilines. Examples of these are 4-amino-N,N-diethylaniline, 3-methyl-4-amino-N,N-diethylaniline, 4-amino-N-ethyl-N-α-hydroxyethylaniline, 3-methyl-4-amino-N-ethyl-N-α-hydroxyethylaniline, 3-methyl-4-amino-N-ethyl-N-α-hydroxyethylaniline, 3-methyl-4-amino-N-ethyl-N-α- methanesulfonamidoethylaniline, 3-methyl-4-amino-N-ethyl-N-α-methoxyethylaniline, 3-α-methanesulfonamidoethyl-4-amino-N,N-diethylaniline, 3-methoxy-4-amino-N-ethyl-N-α-hydroxyethylaniline, 3-methoxy-4-amino-N-ethyl-N-α-methoxyethylaniline, 3-acetamido-4-amino-N,N-diethylaniline, 4-amino-N,N-dimethylaniline, N-ethyl-N-α-[α'-(α''-methoxyethoxy)ethoxy]ethyl-3-methyl-4-aminoaniline, N-ethyl-N-α-(α'-methoxyethoxy)ethyl-3-methyl-4-aminoaniline and the salts of such compounds, such as sulfates, hydrochlorides or toluenesulfonates.

The UV absorbers of the formula Ib used in accordance with the invention can be incorporated alone or together with the colour coupler and, if desired, other additives into the colour-photographic material, by predissolving them in high-boiling organic solvents. It is preferred to use solvents which boil at more than 160° C. Typical examples of such solvents are the esters of phthalic acid, phosphoric acid, citric acid, benzoic acid or of fatty acids, and alkylamides and phenols.

It is usual to use in addition a low-boiling solvent, in order to facilitate the incorporation of the additives into the colour-photographic material. Examples of such solvents are esters such as ethyl acetate, alcohols such as butanol, ketones such as methyl isobutyl ketone, chlorinated hydrocarbons such as methylene chloride, or amides such as dimethylformamide. Where the additives are themselves liquid, they can be incorporated into the photographic material even without the aid of solvents.

The UV absorbers according to the invention may if desired be dispersed in the gelatin layer without oil; Research Disclosure 88/296 017 and 89/303 070.

Further details on high-boiling solvents which can be used can be found in the following publications:

Phosphates: GB-A-791 219, BE-A-755 248, JP-A-76/76 739, 78/27 449, 78/218 252, 78/97 573, 79/148 133, 82/216 177, 82/93 323 and 83/216.177 and EP-A-265 296. Phthalates: GB-A-791 219, JP-A-77/98 050, 82/93 322, 82/216 176, 82/218 251, 83/24 321, 83/45 699, 84/79 888. Amides: GB-A-791 129, JP-A-76/105 043, 77/13 600, 77/61 089, 84/189 556, 87/239 149, U.S. Pat. No. 928,741, EP-A-270 341, WO 88/00 723. Phenols: GB-A-820 329, FR-A-1 220 657, JP-A-69/69 946, 70/3 818, 75/123 026, 75/82 078, 78/17 914, 78/21 166, 82/212 114 and 83/45 699.

Other oxygen-containing compounds: U.S. Pat. Nos. 3,748,141, 3,779,765, JP-A-73/75 126, 74/101 114, 74/10 115, 75/101 625, 76/76 740, 77/61 089, EP-A-304 810 and BE-A-826 039.

Other compounds: JP-A-72/115 369, 72/130 258, 73/127 521, 73/76 592, 77/13 193, 77/36 294, 79/95 233, 91/2 748, 83/105 147 and Research Disclosure 82/21 918.

The quantity of high-boiling solvent is, for example, in the range from 50 mg to 2 g per m² of support, preferably from 200 mg to 1 g per m².

Further preferred colour couplers for use in the compositions according to the invention, examples of such compounds, further additives such as colour fogging inhibitors, DIR couplers and other light stabilizers such as UV absorbers, phenols, phosphorus(III) compounds, organometallic complexes, hydroquinones and hydroquinone ethers, as well as more precise information on the structure of various photographic materials, can be taken from, for example, the publications U.S. Pat. No. 5,300,414 and EP-A-520 938 and the literature cited therein.

The following examples describe the coating compositions according to the invention in more detail without limiting the invention to the examples. In these examples parts and percentages are by weight. Where an example mentions room temperature, this should be understood as meaning a temperature in the range 20–25° C., unless stated otherwise.

A) PREPARATION EXAMPLES

Examples A1 to A3 illustrate the preparation of starting materials.

Example A1

212.6 g (1.0 mol) of 98% 1,3-diphenyl-2-propen-1-one, 249.1 g (2.0 mol) of 98% guanidine nitrate and 1.51 of absolute ethanol are initially introduced at 70° C. 289.2 g (4.0 mol) of 97% potassium methoxide are then added in portions to the white suspension over the course of 40 minutes. After 20 hours at reflux, the yellow suspension is cooled to 50° C. and poured into 6 l of water, extracted with ethyl acetate, and concentrated by evaporation and the residue is recrystallized from isopropanol. 88.1 g of pale yellow crystals are obtained of the compound 1

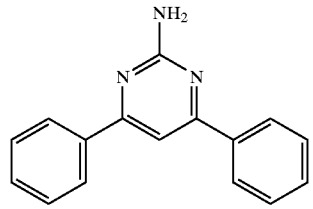

compound 1

(=35.6% yield) with a melting point of 134–136° C.

Example A2

98.9 g (0.4 mol) of 2-amino-4,6-diphenyl-1,3-pyrimidine (compound 1) are introduced into a solution consisting of 1.5 l of water and 1 l of concentrated sulfuric acid. A solution of 75.0 g (1.088 mol) of sodium nitrite in 500 ml of water is added dropwise below the surface of the yellow suspension over the course of 25 hours. After 20 hours at 20–25° C. the yellow suspension is poured into 15 l of water and is rendered alkaline using 2.25 l of 25% aq. ammonia. The product precipitates as a beige solid. It is filtered off, washed with water and dried in a vacuum oven. 88.3 g (=88.9% yield) of beige crystals are obtained of the formula

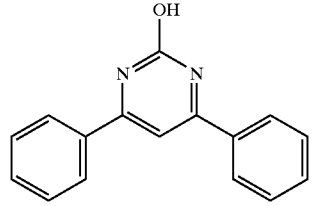

compound 2 with a melting point of 234–236° C.

Example A3

86.9 g (0.35 mol) of 2-hydroxy-4,6-diphenyl-1,3-pyrimidine (compound 2) are stirred in 400 ml (4.38 mol) of phosphoryl chloride under reflux for 6 hours. The reaction mixture is cooled to 20–25° C. and added dropwise to 4 l of water. The beige precipitate is filtered off, washed with water and dried in a vacuum oven. 89.0 g (=95.4% yield) of beige crystals are obtained of the formula

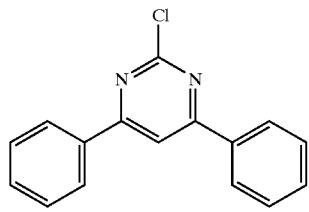

compound 3 with a melting point of 112–114° C.

Examples A4 to A10 and A12 to A13 illustrate the preparation of the compounds according to the invention.

Example A4

40 g (0.15 mol) of 2-chloro-4,6-diphenyl-1,3-pyrimidine (compound 3) are initially introduced together with 22.5 g (0.165 mol) of 98% anhydrous aluminium chloride in 150 ml of a xylene isomer mixture at 70–75° C. 20.0 g (0.18 mol) of 99% analytical-grade resorcinol are added in portions. After 25 hours at reflux, the reaction mixture is poured into 1 l of water. The precipitate is washed with water and decanted. The residue is stirred with 1.5 l of hexane. The fine beige precipitate is filtered off and dried. 46.9 g (=92% yield) of beige crystals are obtained of the formula

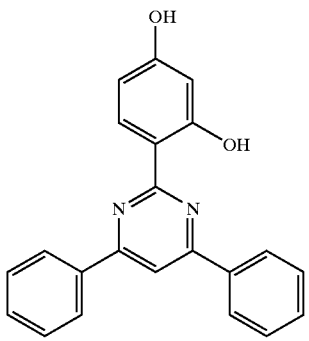

(compound 4) with a melting point of 225–228° C.

The following examples describe the preparation of compounds 5–10 of the general formula

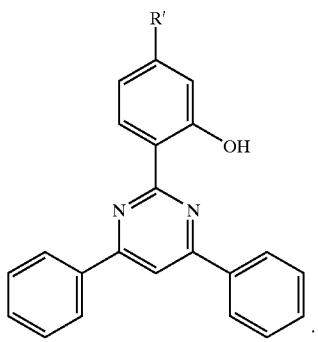

In these examples radicals R' are defined as follows:

Compound 5:

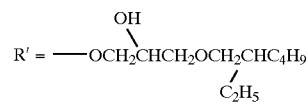

Compound 6: R'=—OC$_6$H$_{13}$

Compound 7: R'=—O—CH$_2$—COOC$_2$H$_5$

Compound 8: R'=—O—CH(C$_6$H$_{13}$)—COOC$_8$H$_{17}$

Compound 9: R'=—O—CH$_2$—CH(OH)—CH$_2$—O—C$_{14}$H$_{29}$

Compound 10:

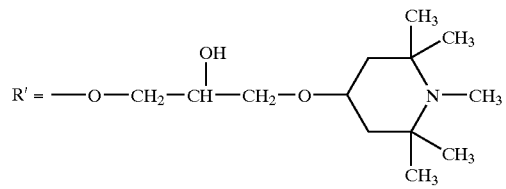

Example A5

3.4 g (0.01 mol) of 2-(2',4'-dihydroxyphenyl)-4,6-diphenyl-1,3-pyrimidine (compound 4) are stirred together with 2.1 g (0.011 mol) of 2-ethylhexyl glycidyl ether and 0.2 g (0.0005 mol) of ethyltriphenylphosphonium bromide for 30 minutes at 150° C. The reaction mixture is cooled to 110° C. 25 ml of toluene and 0.25 g of bleaching earth (Prolith Rapid®) are added thereto and the mixture is filtered while hot over kieselguhr. The clear yellow solution is subjected to fractional filtration over silica gel 60 (particle size 60–230 μm; Merck, Darmstadt), using toluene as eluent.

The clear yellow oil is stirred with hexane, the product crystallizing out. 3.8 g (=71.7% yield) of pale yellow crystals are obtained, m.p. 67–69° C. (compound 5).

Example A6

6.0 ml (0.042 mol) of 1-bromohexane are added at room temperature to a mixture of 13.6 g (0.04 mol) of compound 4, 5.8 g (0.042 mol) of potassium carbonate and 100 ml of DMF. The mixture is stirred at 130° C. for 5 hours, and is then cooled to room temperature and poured into 1 l of H$_2$O. The crystalline product is filtered off and recrystallized from hexane. Compound 6 is obtained (R'=—OC$_6$H$_{13}$), m.p. 103–107° C.

Example A7

13.6 g (0.04 mol) of compound 4 are placed in 120 ml of absolute ethanol, and 11.2 g (0.10 mol) of potassium tert-butoxide are added. 8.5 ml (0.08 mol) of ethyl chloroacetate are added to the yellow suspension at 20° C. over the course of 5 minutes. The mixture is held at reflux temperature with stiring for 24 h. After cooling to room temperature, it is poured into 1.5 l of H$_2$O. The crystalline product is filtered off and recrystallized from ethanol. Compound 7 is obtained (R'=O—CH$_2$—COOC$_2$H$_5$), m.p. 138–140° C.

Example A8

6.8 g (0.02 mol) of compound 4 and 0.1 g of potassium iodide are added at 110° C. to 2.8 g (0.02 mol) of potassium carbonate in 50 ml of diethylene glycol dimethyl ether (diglyme). 6.4 g (0.022 mol) of 1-octyloxycarbonylheptyl bromide are added to the solution over the course of 20 minutes. The mixture is stirred at 120° C. for 7 h. After cooling to room temperature, the suspension is poured into 500 ml of H₂O, the product is extracted with ethyl acetate and the organic phase is evaporated. Compound 8 is obtained (R'=—O—CH(C₆H₁₃)—COOC₈H₁₇) as a yellow liquid. Mass spectrometry: M⁺=594 g/mol

| Elemental analysis: | | | | | |
|---|---|---|---|---|---|
| calculated | % C | 76.7 | found | % C | 76.1 |
| | % H | 7.8 | | % H | 7.9 |
| | % N | 4.7 | | % N | 4.6 |

Example A9

8.5 g (0.025 mol) of compound 4, 8.05 g (0.0275 mol) of tetradecyl glycidyl ether and 0.46 g (0.00125 mol) of ethyltriphenylphosphonium bromide are stirred at 150° C. for 3 hours. After cooling to room temperature, the clear, dark red melt is admixed with 15 ml of toluene. The catalyst is washed out with water. The product crystallizes slowly. Compound 9 is obtained (R'=—O—CH₂—CH(OH)—CH₂—O—C₁₄H₂₉) as a beige product, melting point 68–69° C.

| Elemental analysis: | | | | | |
|---|---|---|---|---|---|
| calculated | % C | 76.69 | found | % C | 76.51 |
| | % H | 8.25 | | % H | 8.28 |
| | % N | 4.59 | | % N | 4.59 |

Example A10

10.2 g (0.03 mol) of compound 4, 7.7 g (0.033 mol) of 1,2,2,6,6-pentamethyl-4-(oxiran-2-ylmethoxy)piperidine and 0.56 g (0.0015 mol) of ethyltriphenylphosphonium bromide are stirred at 150° C. for 2.5 hours. After cooling to room temperature, the reaction mixture is dissolved in 70 ml of ethyl acetate, subjected to a claifying filtration and concentrated by evaporation. The yellow solid obtained is recrystallized from acetonitrile. Compound 10 is obtained

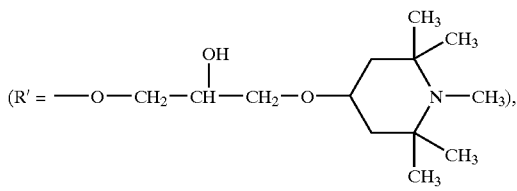

melting point 167–170° C.
Mass spectrometry: M⁺=568 g/mol; molecular weight 567.73 g/mol.

| Elemental analysis: | | | | | |
|---|---|---|---|---|---|
| calculated | % C | 74.05 | found | % C | 73.93 |
| | % H | 7.28 | | % H | 7.34 |
| | % N | 7.40 | | % N | 7.37 |

Example A11

Preparation of Intermediates of the Formula

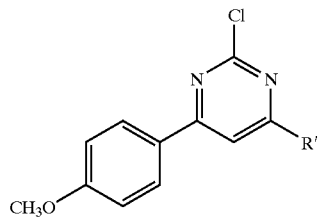

in which R' is 4-methoxyphenyl (compound 11a) or in which R' is Cl (compound 11b).

A solution of 4-methoxyphenylmagnesium bromide (prepared from 37.4 g [0.2 mol] of 4-bromoanisole and 4.9 g [0.2 mol] of iodine-activated magnesium turnings in 50 ml of tetrahydrofuran (THF)) is added dropwise under nitrogen and over the course of one hour to a solution of 18.3 g (=0.1 mol) of 2,4,6-trichloropyrimidine in 65 ml of anhydrous THF, the temperature of the mixture being maintained within the range from 0 to 20° C. After addition is complete the mixture is stirred at 20° C. for a further 48 hours, and is then diluted with 90 ml of toluene and poured into 90 ml of 12% aqueous HCl. The organic phase is separated off, washed to neutrality with water and concentrated in a rotary evaporator. The brown oil obtained (34 g) is separated by column chromatography on 500 g of SiO₂ (30–63 μm); the eluent is toluene/hexane, 60:40 to 100:0. Compounds 11a and 11b of the formula above are obtained;

2-chloro-4,6-bis(4-methoxyphenyl)pyrimidine (11a; R'=4-methoxyphenyl), melting point 187–189° C. and 2,4-dichloro-6-(4-methoxyphenyl)pyrimidine (11b; R'=Cl), melting point 86–89° C.

Example A12

In analogy to the method described in Example A4, compound 11a obtained in Example A11 is reacted with 1.2 equivalents of 99% analytical-grade resorcinol. Compound 12 of the formula

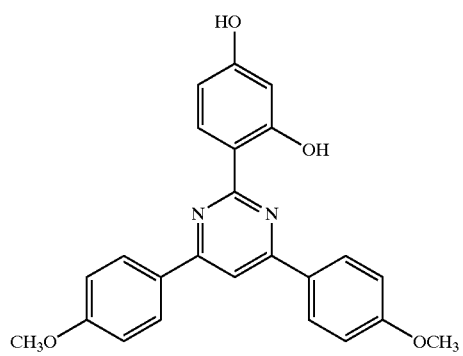

is obtained.

Example A13

In analogy to the method described in Example A4, compound 11b obtained in Example A11 is reacted with 2.4 equivalents of 99% analytical-grade resorcinol. Compound 13 of the formula

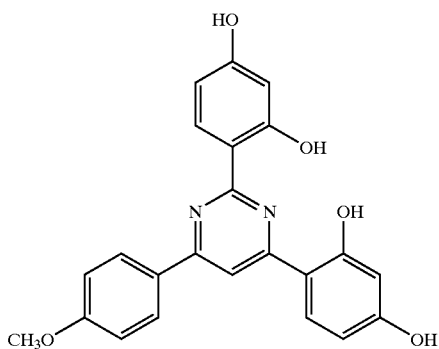

is obtained.

B) APPLICATION EXAMPLES

Example B1

Stabilization of a 2-coat Metallic Finish

The light stabilizers are incorporated into 5–10 g of xylene and tested in a clearcoat of the following composition:

| | |
|---|---|
| Synthacryl ® SC 303[1] | 27.51 |
| Synthacryl ® SC 370[2] | 23.34 |
| Maprenal ® MF 650[3] | 27.29 |
| Butyl acetate/butanol (37:8) | 4.33 |
| Isobutanol | 4.87 |
| Solvesso ® 150[4] | 2.72 |
| Kristallöl K-30[5] | 8.74 |
| Levelling assistant Baysilon ® MA[6] | 1.20 |
| | 100.00 g |

[1]Acrylate resin from Hoechst AG; 65% solution in 26:9 xylene/butanol
[2]Acrylate resin from Hoechst AG; 75% solution in Solvesso ® 100[4]
[3]Melamine resin from Hoechst AG; 55% solution in isobutanol
[4]Manufactured by ESSO
[5]Manufactured by Shell
[6]Manufactured by Bayer AG; 1% in Solvesso ® 150

2% of stabilizer is added to the clearcoat, based on the solids content of the coating material. A number of additional coating samples are prepared which contain, in addition to the stabilizer according to the invention, 0.7% of the compound

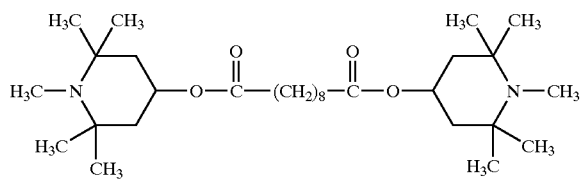

(compound A) based on the solids content of the coating material. The control is a clearcoat containing no light stabilizer.

The clearcoat is diluted to spray viscosity with Solvesso® 100 and is sprayed onto an aluminium panel which has been pretreated (coil coat, filler, silver metallic basecoat) and baked at 130° C. for 30 minutes. The resulting dry film thickness of the clearcoat is 40–50 $\mu$m.

The samples are then weathered in a UVCON® weathering instrument from Atlas Corp. (UVB-313 lamps) at a cycle of 8 h UV irradiation at 70° C. and 4 h condensation at 50° C.

The surface gloss (20° gloss in accordance with DIN 67 530) of the samples is measured at regular intervals. The results of these measurements are compiled in Table 1.

TABLE 1

20° gloss in accordance with DIN 67 530 before and after weathering

| Stabilizer | 20° gloss after weathering for | | | | | | | |
|---|---|---|---|---|---|---|---|---|
| | 0 | 800 | 1200 | 1600 | 2000 | 2400 | 2800 | 3200 h |
| none | 90 | 67 | 21* | | | | | |
| 2% comp. 6 | 91 | 92 | 91 | 90 | 42* | | | |
| 2% comp. 7 | 91 | 93 | 92 | 80 | 23* | | | |
| 2% comp. 8 | 91 | 92 | 92 | 89 | 35* | | | |
| 2% comp. 5 + 0,7% A | 92 | 90 | 90 | 89 | 90 | 90 | 89 | 83 |
| 2% comp. 6 + 0,7% A | 90 | 93 | 91 | 90 | 91 | 91 | 91 | 78 |
| 2% comp. 7 + 0,7% A | 90 | 92 | 88 | 90 | 91 | 90 | 90 | 90 |
| 2% comp. 8 + 0,7% A | 90 | 92 | 91 | 90 | 91 | 90 | 90 | 87 |

*cracking

The stabilized sample has a better weathering stability (gloss retention, crack resistance) than the non-stabilized comparison sample.

Example B2

Stabilization of Polycarbonate 10 g of polycarbonate powder (Lexan® 115) are dissolved with stirring at room temperature in 50 g of methylene chloride, which requires several hours. To this solution is added 0.2 g of UV absorber, corresponding to 2% additional concentration. These solutions are used to cast films 20 $\mu$m thick.

The films are exposed in an Atlas Weatherometer CI 65 at a black-panel temperature of 63° C. and a relative humidity of 60%. Before beginning the exposure experiments, the initial colour ($YI_{AZ}$) and subsequently, at regular intervals, the discolouration of the samples are tested by measuring the Yellowness Index (YI, method ASTM D 1925). Table 2 indicates the initial colour ($YI_{AZ}$). The films are exposed further until they become brittle, which is evident by the formation of cracks in the films.

TABLE 2

Initial colour (Yellowness Index before weathering; $YI_{AZ}$)

| UV absorber | $YI_{AZ}$ |
|---|---|
| none | 0.1 |
| 2% compound 6 | 0.4 |
| 2% compound 7 | 0.3 |

The samples stabilized with the compounds according to the invention show practically no discolourations in comparison with the non-stabilized sample before the beginning of weathering. The exposure experiments show that the substrate is given outstanding protection against discolouration and embrittlement by the compounds according to the invention.

Example B3

Inherent Stability in a Photographic Layer 43.7 mg of compound 5 are dissolved in 2 ml of ethyl acetate which contains tricresyl phosphate in a concentration of 24 g/l. 1 ml of this solution is mixed with 9 ml of a solution containing, per liter, 27.6 g of gelatin and 6.8 g of an 8% aqueous solution of sodium 4,8-diisobutylnaphthalene-2-sulfonate as wetting agent. The mixture is homogeneously emulsified for 3 min in an ultrasound bath. Subsequently, 7.5 ml of the resulting emulsion are mixed with 4.5 ml of an aqueous curing solution comprising 0.24% of the potassium salt of 2-hydroxy-4,6-dichloro-1,3,5-triazine. 8 ml in each case of this emulsion are applied to polyester films with dimensions of 13×18 cm, corresponding to a UV absorber concentration of 0.467 g/m$^2$.

The samples are dried at room temperature for 7 days. The optical density at the absorption maximum is then determined using a UV-VIS spectrophotometer.

The samples are exposed in an Atlas Weatherometer CI 35 at a black-panel temperature of 62° C. and a relative humidity of 50%. After an exposure duration corresponding to 60 kJ/cm$^2$ the optical density is again measured at unchanged wavelength, and the loss of optical density as a result of exposure is determined from this measurement.

In the case of the sample stabilized with compound 5, the loss of optical density is 2.1%.

The stabilizer according to the invention thus possesses outstanding light fastness in photographic layers.

Example B4

Stabilization of Polyamide

Polyamide 6 powder (Ultramid® B3S, manufactured by BASF) is mixed dry together with stabilizers according to the invention for 2 minutes in a Henschel mixer and then processed in a Berstorff twin-screw extruder at a speed of 95/min and at a temperature setting of 230° C./235° C./240° C./240° C. The quantities of stabilizer are given in % by weight, based on the quantity of polyamide employed. Using an injection moulding unit (model Arburg L, composition temperature 240° C., mould temperature 80° C.) 2 mm thick plates are produced from each mixture. For comparison, a further sample is produced without stabilizers according to the invention.

The plates are exposed in an Atlas Weatherometer CI 65 at a black-panel temperature of 63° C. and a relative humidity of 60%, using a water spray cycle of 102 min dry/18 min wet. The time for cracks to become visible on the plates is measured.

As well as the abovementioned stabilizers according to the invention, the following additional stabilizers are employed:

A N,N'-bis[3-(3',5'-di-tert-butyl-4'-hydroxyphenyl) propionyl]hexamethylenediamine,
B tris(2,4-di-tert-butylphenyl)phosphite,
C the condensation product of N,N'-bis(2,2,6,6-tetramethyl-4-piperidyl)hexamethylene-diamine and 4-tert-octylamino-2,6-dichloro-1,3,5-s-triazine having a melting point of 120–150° C.

The samples stabilized according to the invention show a very good resistance to the appearance of cracks.

What is claimed is:
1. A compound of the formula Ib

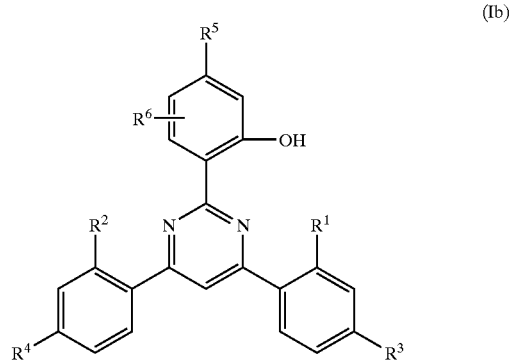

in which
R$^1$ and R$^2$ independently of one another are H; OH; C$_1$–C$_{12}$alkyl; cyclohexyl or trifluoromethyl;
R$^3$ and R$^4$ independently of one another are hydrogen; —OH; C$_1$–C$_3$alkyl; C$_1$–C$_3$alkoxy; or halogen or have one of the definitions of R$^7$ or are OR$^7$;
R$^5$ has one of the definitions given for R$^7$ or is halogen; C$_1$–C$_3$alkyl; —O—CO—R$^{12}$; —O—SO$_2$—R$^{13}$ or —O—R$^7$;
R$^6$ is H; C$_2$–C$_{18}$alkenyl; —X—Z$^3$; benzoyl which is unsubstituted or substituted on the phenyl ring by methyl, halogen, —CN or methoxy; —C(Z$^3$)=N—Z$^3$; —CH(Z$^3$)—NH—Z$^3$; a radical of the formula

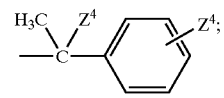

or a radical of the formula

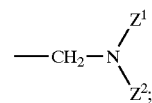

R$^7$ is C$_4$–C$_{18}$alkyl or C$_2$–C$_{18}$alkenyl or C$_5$–C$_{18}$alkyloxycarbonyl; or R$^7$ is C$_1$–C$_{18}$alkyl which is substituted by a radical selected from the group consisting of OH, C$_1$–C$_{18}$alkoxy, C$_2$–C$_{18}$alkanoyl, halogen, —COOH, —COOR$^8$, —CONH$_2$, —CONHR$^9$, —CON(R$^9$)(R$^{10}$), —NH$_2$, —NHR$^9$, —N(R$^9$)(R$^{10}$), —NHCOR$^{11}$, —CN, —OCOR$^{11}$, a radical of the formula

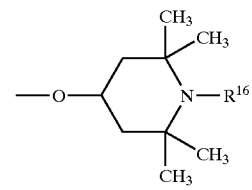

and phenoxy which is unsubstituted or is substituted by C$_1$–C$_{18}$alkyl, C$_1$–C$_{18}$alkoxy or halogen; or R$^7$ is C$_4$–C$_{20}$alkyl which is interrupted by O and substituted by OH or C$_1$–C$_{12}$alkoxy; glycidyl; C$_5$–C$_8$cycloalkyl;

cyclohexyl which is substituted by OH, $C_1$–$C_4$alkyl or —OCOR$^{11}$; or $C_7$–$C_{11}$-phenylalkyl which is unsubstituted or substituted by OH, Cl or CH$_3$;

R$^8$ is $C_1$–$C_{18}$alkyl; $C_2$–$C_6$-hydroxyalkyl; $C_3$–$C_{18}$alkenyl; $C_3$–$C_{20}$alkyl which is interrupted by O, N or S and is unsubstituted or is substituted by OH; $C_1$–$C_4$alkyl which is substituted by a radical selected from the group consisting of —P(O)(OR$^{14}$)$_2$, —N(R$^9$)(R$^{10}$), —OCOR$^{11}$ and OH; glycidyl; cyclohexyl or $C_7$–$C_{11}$phenylalkyl; or is a group of the formula

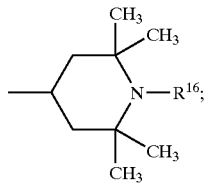

R$^9$ and R$^{10}$ independently of one another are $C_1$–$C_{12}$alkyl; $C_3$–$C_{12}$alkoxyalkyl; $C_4$–$C_{16}$dialkylaminoalkyl or $C_5$–$C_{12}$cycloalkyl or R$^9$ and R$^{10}$ together are $C_3$–$C_9$alkylene or -oxaalkylene or -azaalkylene;

R$^{11}$ is $C_1$–$C_{18}$alkyl; $C_2$–$C_{18}$alkenyl or phenyl;

R$^{12}$ is $C_1$–$C_{18}$alkyl; $C_2$–$C_{18}$alkenyl; phenyl; or —R$^{15}$—O—CO—R$^{11}$; or is a group of the formula

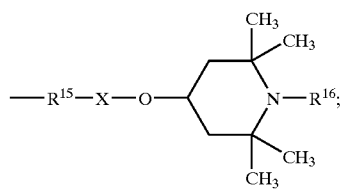

R$^{13}$ is $C_1$–$C_{12}$alkyl; phenyl; naphthyl or $C_7$–$C_{14}$alkylphenyl; and R$^{14}$ is $C_1$–$C_{12}$alkyl or phenyl;

R$^{15}$ is $C_1$–$C_{18}$alkylene or $C_2$–$C_{18}$alkenylene;

R$^{16}$ is hydrogen; oxide; $C_1$–$C_8$alkanoyl; $C_1$–$C_{18}$alkyl; $C_2$–$C_{18}$hydroxyalkyl; $C_3$–$C_{18}$hydroxyalkyl which is interrupted by O; $C_1$–$C_{18}$-alkoxy; $C_5$–$C_8$cycloalkyl; $C_5$–$C_8$-cycloalkoxy; $C_7$–$C_{11}$phenylalkyl; $C_7$–$C_{11}$phenylalkyl which is substituted on the phenyl ring by from 1 to 3 radicals $C_1$–$C_4$alkyl or $C_1$–$C_8$alkanoyl; or $C_7$–$C_{11}$phenylalkoxy;

X is a direct bond or —CO—;

Z$^1$ and Z$^2$ independently of one another are $C_1$–$C_{12}$alkyl or together are $C_4$–$C_{10}$alkylene which may be interrupted by an oxygen atom;

Z$^3$ is $C_1$–$C_{20}$-Alkyl; and

Z$^4$ is hydrogen or methyl;

with the exception of a compound of the formula Ib in which 2 of the radicals R$^3$, R$^4$ and R$^5$ are alkoxy and the third radical has a definition other than alkoxy.

2. A compound of the formula Ib according to claim 1, in which

R$^1$ and R$^2$ independently of one another are H; OH; $C_1$–$C_{12}$alkyl; cyclohexyl or trifluoromethyl;

R$^3$ and R$^4$ independently of one another are hydrogen; —OH; $C_1$–$C_8$alkyl; $C_1$–$C_{18}$alkoxy; or halogen or may have one of the definitions of R$^7$;

R$^5$ has one of the definitions given for R$^7$ or is halogen; —O—CO—R$^{12}$; —O—SO$_2$—R$^{13}$ or —O—R$^7$;

R$^6$ is H or $C_1$–$C_{12}$alkyl;

R$^7$ is $C_2$–$C_{18}$alkenyl; or R$^7$ is $C_1$–$C_{12}$alkyl which is substituted by a radical selected from the group consisting of OH, $C_1$–$C_{18}$alkoxy, halogen, —COOH, —COOR$^8$, —CONH$_2$, —CONHR$^9$, —CON(R$^9$)(R$^{10}$), —NH$_2$, —NHR$^9$, —N(R$^9$)(R$^{10}$), —NHCOR$^{11}$, —CN, —OCOR$^{11}$ and phenoxy which is unsubstituted or is substituted by $C_1$–$C_{18}$alkyl, $C_1$–$C_{18}$alkoxy or halogen; or R$^7$ is $C_4$–$C_{20}$alkyl which is interrupted by O and substituted by OH or $C_1$–$C_{12}$alkoxy; glycidyl; $C_5$–$C_8$cycloalkyl; cyclohexyl which is substituted by OH, $C_1$–$C_4$alkyl or —OCOR$^{11}$; or $C_7$–$C_{11}$phenylalkyl which is unsubstituted or substituted by OH, Cl or CH$_3$;

R$^8$ is $C_1$–$C_{18}$alkyl; $C_2$–$C_6$hydroxyalkyl; $C_3$–$C_{18}$alkenyl; $C_3$–$C_{20}$alkyl which is interrupted by O, N or S and is unsubstituted or is substituted by OH; $C_1$–$C_4$alkyl which is substituted by a radical selected from the group consisting of —P(O)(OR$^{14}$)$_2$, —N(R$^9$)(R$^{10}$), —OCOR$^{11}$ and OH; glycidyl; cyclohexyl or $C_7$–$C_{11}$phenylalkyl;

R$^9$ and R$^{10}$ independently of one another are $C_1$–$C_{12}$alkyl; $C_3$–$C_{12}$alkoxyalkyl; $C_4$–$C_{16}$-dialkylaminoalkyl or $C_5$–$C_{12}$cycloalkyl or R$^9$ and R$^{10}$ together are $C_3$–$C_9$alkylene or -oxaalkylene or -azaalkylene;

R$^{11}$ is $C_1$–$C_{18}$alkyl; $C_2$–$C_{18}$alkenyl or phenyl;

R$^{12}$ is $C_1$–$C_{18}$alkyl; $C_2$–$C_{18}$alkenyl; phenyl; or —R$^{15}$—O—CO—R$^{11}$; or is a group of the formula

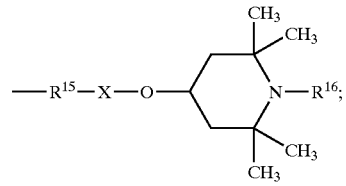

R$^{13}$ is $C_1$–$C_{12}$alkyl; phenyl; naphthyl or $C_7$–$C_{14}$alkylphenyl; and R$^{14}$ is $C_1$–$C_{12}$alkyl or phenyl;

R$^{15}$ is $C_1$–$C_{18}$alkylene or $C_2$–$C_{18}$alkenylene;

R$^{16}$ is hydrogen; $C_1$–$C_8$alkanoyl; $C_1$–$C_{18}$alkyl; $C_1$–$C_{18}$alkoxy; $C_5$–$C_8$cycloalkyl; $C_5$–$C_8$cycloalkoxy; $C_7$–$C_{11}$phenylalkyl; $C_7$–$C_{11}$phenylalkyl which is substituted on the phenyl ring by from 1 to 3 radicals $C_1$–$C_4$alkyl or $C_1$–$C_8$alkanoyl; or $C_7$–$C_{11}$phenylalkoxy; and X is a direct bond or —CO—.

3. A compound of the formula Ib according to claim 1, in which

R$^1$ and R$^2$ independently of one another are hydrogen or $C_1$–$C_4$alkyl;

R$^3$ and R$^4$ independently of one another are hydrogen; $C_1$–$C_3$alkyl; $C_1$–$C_3$alkoxy or halogen or have one of the definitions of R$^7$ or are OR$^7$;

R$^5$ has one of the definitions given for R$^7$ or is halogen; —O—CO—R$^{12}$ or —O—R$^7$;

R$^6$ is in the o-position to R$^5$ and in the p-position to —OH and is hydrogen, $C_1$–$C_6$alkyl, allyl, $C_6$–$C_{18}$alkanoyl, benzoyl or α-methylbenzyl;

R$^7$ is $C_4$–$C_{18}$alkyl or $C_2$–$C_{18}$alkenyl; or R$^7$ is $C_1$–$C_{12}$alkyl which is substituted by a radical selected from the group consisting of OH, $C_1$–$C_{18}$alkoxy, —COOR$^8$, a radical of the formula

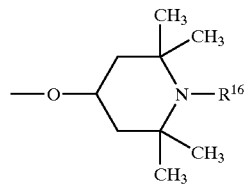

and —OCOR$^{11}$; or R$^7$ is $C_7$–$C_{18}$alkyl which is interrupted by from 1 to 6 —O— and substituted by OH; $C_5$–$C_8$cycloalkyl; or $C_7$–$C_{11}$phenylalkyl;

R$^8$ is $C_1$–$C_{18}$alkyl; $C_3$–$C_{18}$alkenyl or a group of the formula

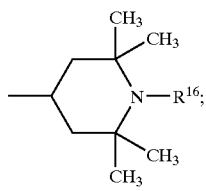

R$^{11}$ is $C_1$–$C_{18}$alkyl or $C_2$–$C_{18}$alkenyl;

R$^{12}$ is $C_1$–$C_{18}$alkyl; $C_2$–$C_{18}$alkenyl; —R$^{15}$—O—CO—CH=CH$_2$; or —R$^{15}$—O—CO—C(CH$_3$)=CH$_2$; or is a group of the formula

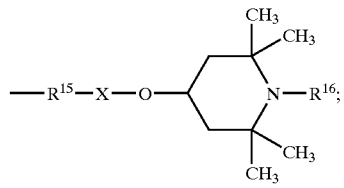

R$^{15}$ is $C_2$–$C_{18}$alkylene; and

R$^{16}$ is hydrogen; oxide; $C_2$–$C_8$alkanoyl; $C_1$–$C_{12}$alkyl; hydroxyethyl; $C_1$–$C_{18}$alkoxy; $C_5$–$C_8$cycloalkyl; $C_5$–$C_8$cycloalkoxy; or $C_7$–$C_{11}$phenylalkyl.

4. A compound of the formula Ib according to claim 1, in which

R$^1$ and R$^2$ independently of one another are hydrogen or $C_1$–$C_4$alkyl;

R$^3$ and R$^4$ independently of one another are hydrogen or $C_1$–$C_4$alkoxy or $C_1$–$C_4$alkyl;

R$^5$ is —O—R$^7$;

R$^6$ is in the o-position to R$^5$ and in the p-position to OH and is hydrogen or $C_1$–$C_6$alkyl or allyl;

R$^7$ is $C_4$–$C_{18}$alkyl or $C_3$–$C_{18}$alkenyl; or R$^7$ is $C_1$–$C_{12}$alkyl which is substituted by a radical selected from the group consisting of OH, $C_1$–$C_{18}$alkoxy, —COOR$^8$, a radical of the formula

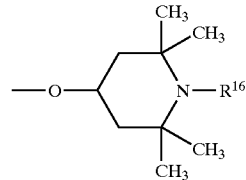

and —OCOR$^{11}$;

R$^8$ is $C_1$–$C_{18}$alkyl;

R$^{11}$ is $C_1$–$C_{18}$alkyl or $C_2$–$C_3$alkenyl.

5. A composition comprising
   A) an organic material which is sensitive to damage by light, oxygen and/or heat, and
   B) as stabilizer, a compound of the formula Ib according to claim 1.

6. A composition according to claim 5, in which component A is a photographic material or a thermoplastic polymer which contains a heteroatom selected from nitrogen, oxygen and sulfur in the principal chain.

7. A composition according to claim 6 in which component A is polycarbonate.

8. A composition according to claim 5 comprising from 0.01 to 15 parts by weight of component B per 100 parts by weight of component A.

9. A composition according to claim 5 comprising, in addition to components A and B, another stabilizer or other additive.

10. A method of stabilizing organic material against damage by light, oxygen and/or heat, which comprises adding to this material a compound of the formula Ib according to claim 1 as stabilizer.

11. A shaped article comprising
    A) a synthetic organic polymer which is sensitive to damage by light, oxygen and/or heat, and
    B) a compound of the formula Ib according to claim 1.

12. A shaped article according to claim 11 which is a multilayer system, wherein an external layer having a thickness of 10–100 μm comprises component (B) whereas the inner layer contains little or no compound of component(B).

* * * * *